United States Patent [19]
Svenson et al.

[11] Patent Number: 6,026,173
[45] Date of Patent: *Feb. 15, 2000

[54] ELECTROMAGNETIC IMAGING AND THERAPEUTIC (EMIT) SYSTEMS

[76] Inventors: Robert H. Svenson; Serguei Y. Semenov; Vladimir Baranov, all of c/o The Carolinas Heart Institute, 1000 Blythe Blvd., Charlotte, N.C. 29232

[*] Notice: This patent is subject to a terminal disclaimer.

[21] Appl. No.: 08/896,525

[22] Filed: Jul. 5, 1997

[51] Int. Cl.⁷ ........................................................ G06K 9/00
[52] U.S. Cl. ........................... 382/131; 600/425; 324/637
[58] Field of Search ................................. 600/425, 430, 600/429; 73/601, 602, 620; 382/128, 131; 324/637, 638, 639

[56] References Cited

U.S. PATENT DOCUMENTS

| | | | |
|---|---|---|---|
| 4,798,209 | 1/1989 | Klingenbeck | 600/430 |
| 5,263,050 | 11/1993 | Guo et al. | 600/425 |
| 5,715,819 | 2/1998 | Svenson et al. | 600/425 |

FOREIGN PATENT DOCUMENTS 9532665  12/1995  WIPO .

*Primary Examiner*—Amelia Au
*Assistant Examiner*—Jingge Wu
*Attorney, Agent, or Firm*—Patterson & Keough, P.A.

[57] ABSTRACT

The invention is a system and method for non-invasive tomographic spectroscopy of tissue using a plurality of microwave emitter-receivers spatially oriented to the tissue, an interface medium placed between the emitter-receivers, and a control subsystem operably coupled to the plurality of emitter-receivers for selectively controlling power to the plurality of emitter-receivers and for receiving signals from the plurality of emitter-receivers so that multiple frequency radiation is emitted from a selected plurality of emitter-receivers and received by a selected plurality of emitter-receivers after interacting with and passing through the tissue, and a computational subsystem operably connected to the control subsystem for computing a tomographic spectroscopic image of the tissue from the microwave signals received from the selected plurality of emitter-receivers.

2 Claims, 24 Drawing Sheets

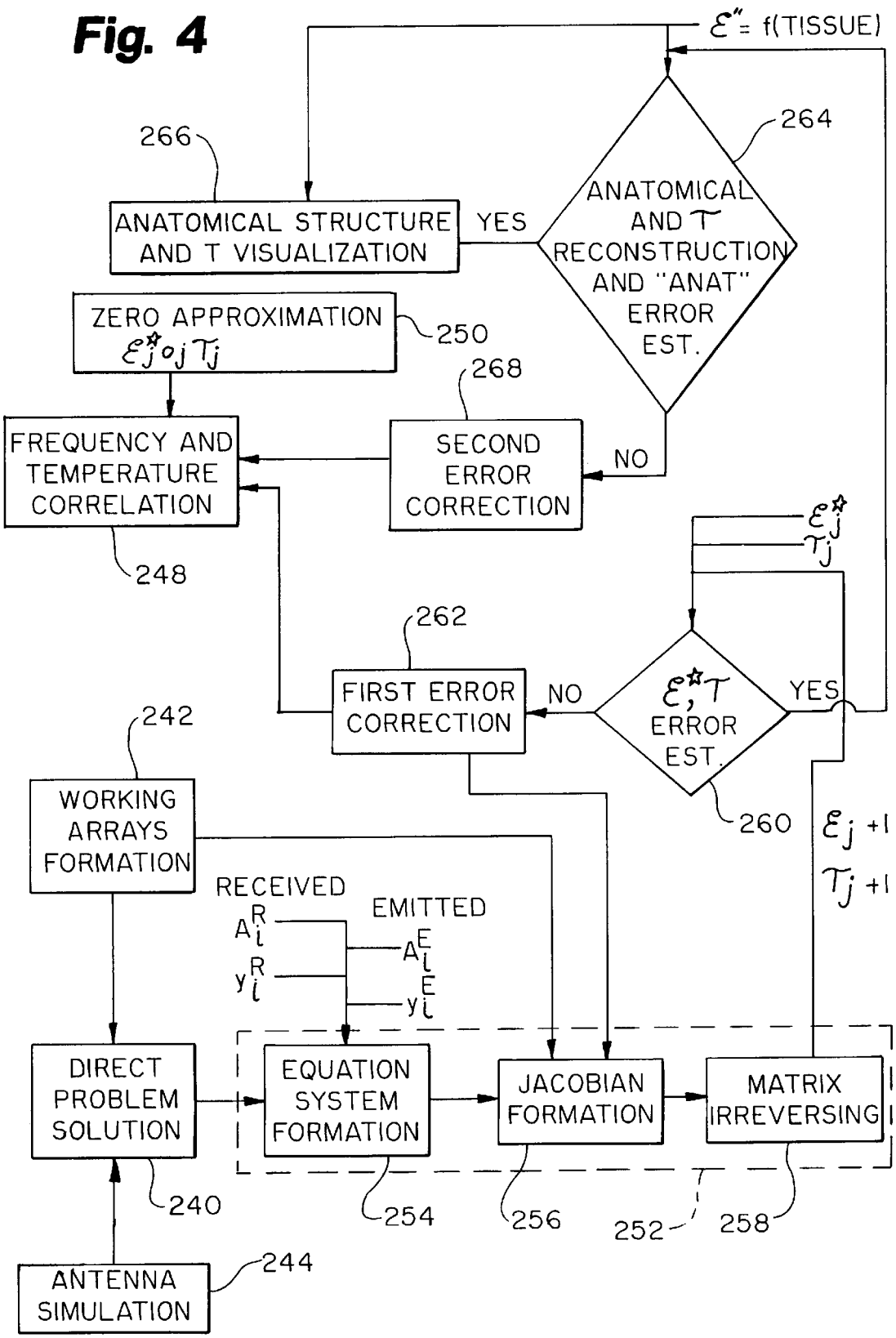

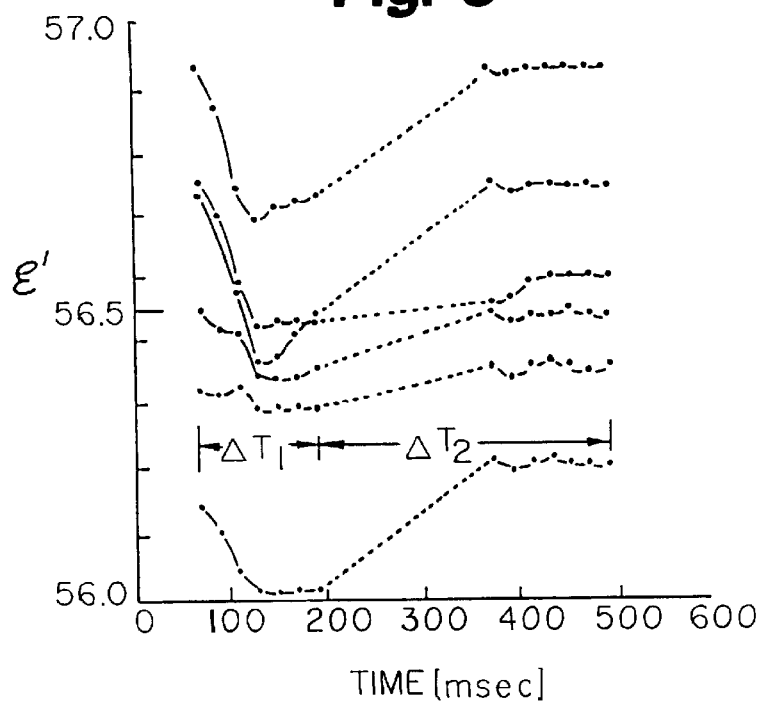
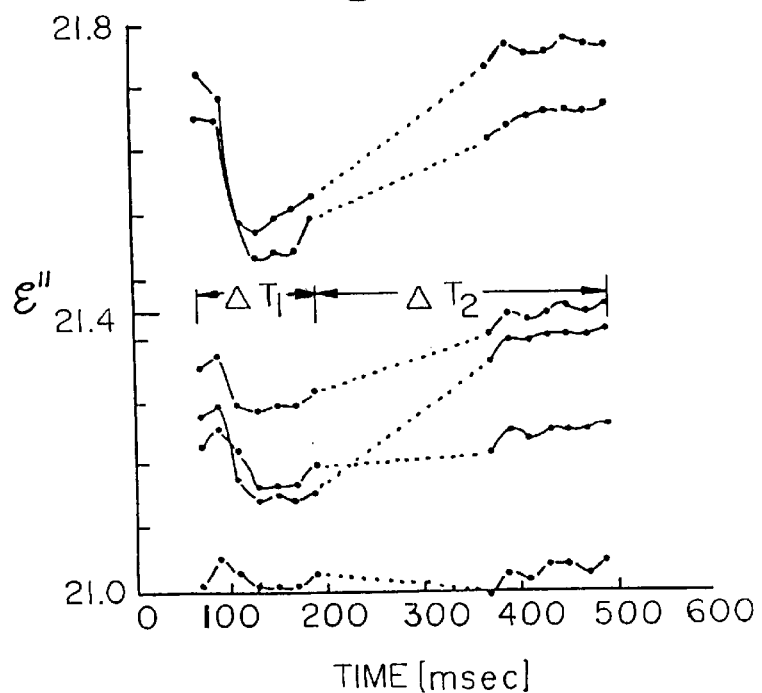

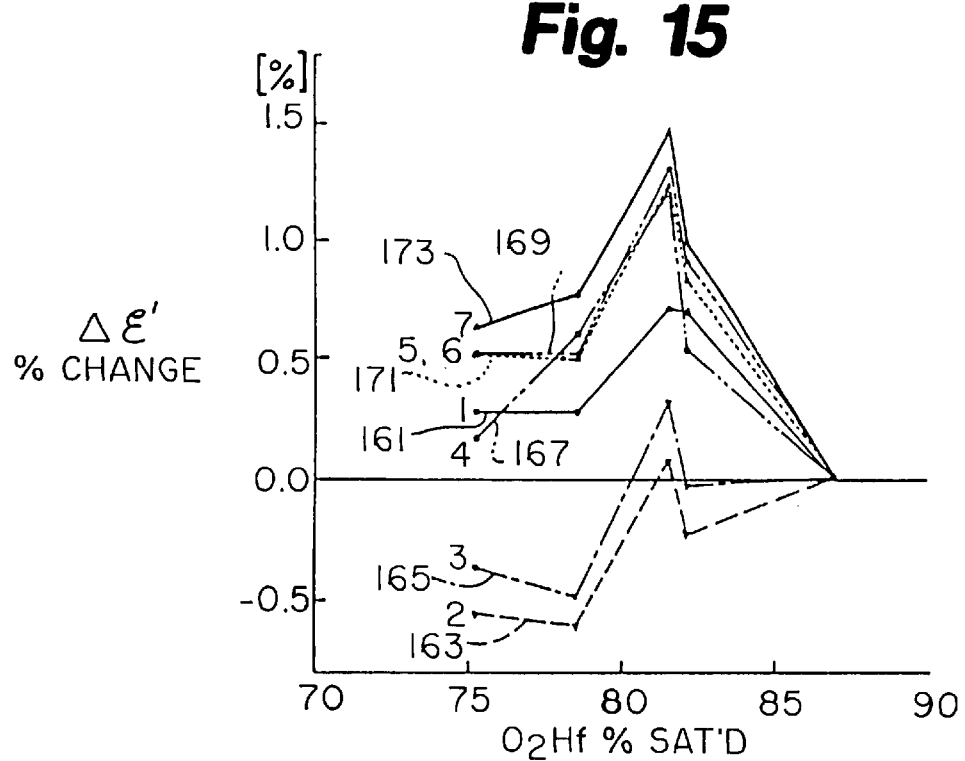
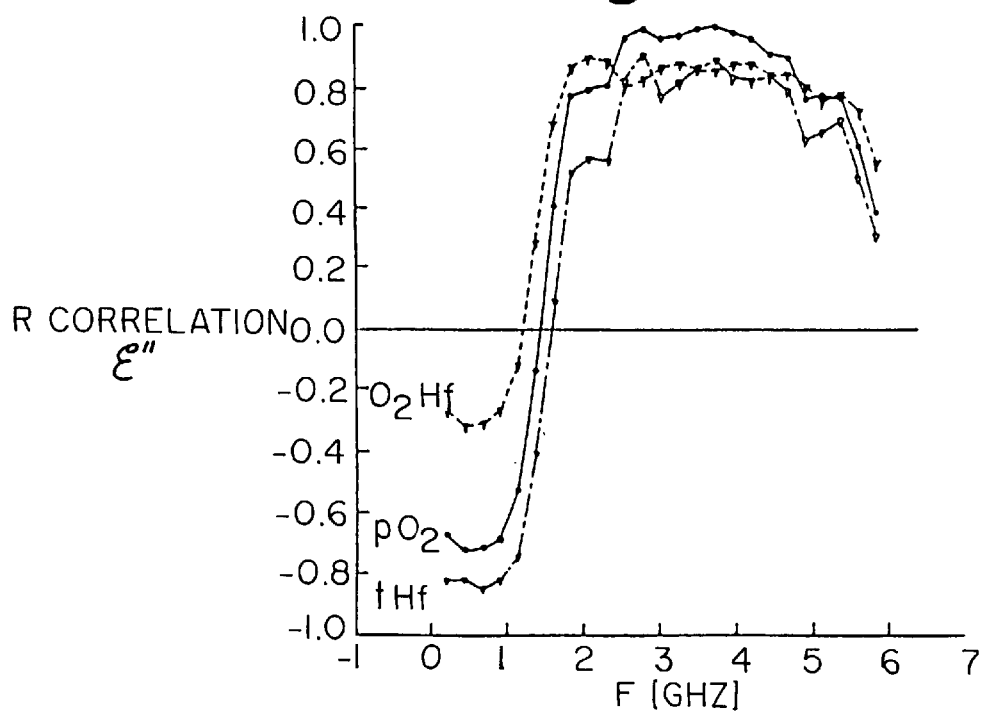

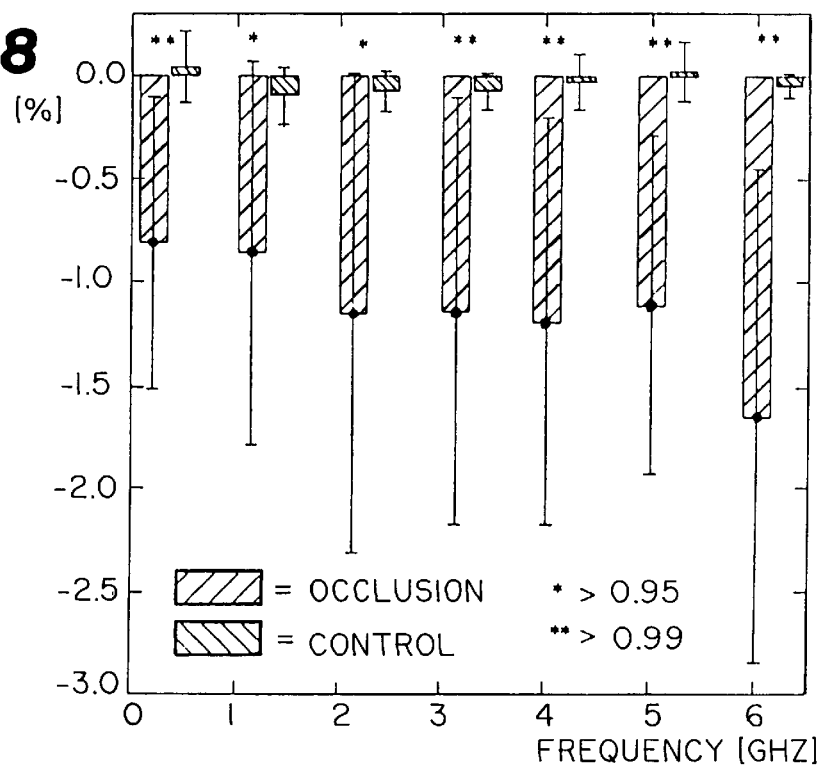
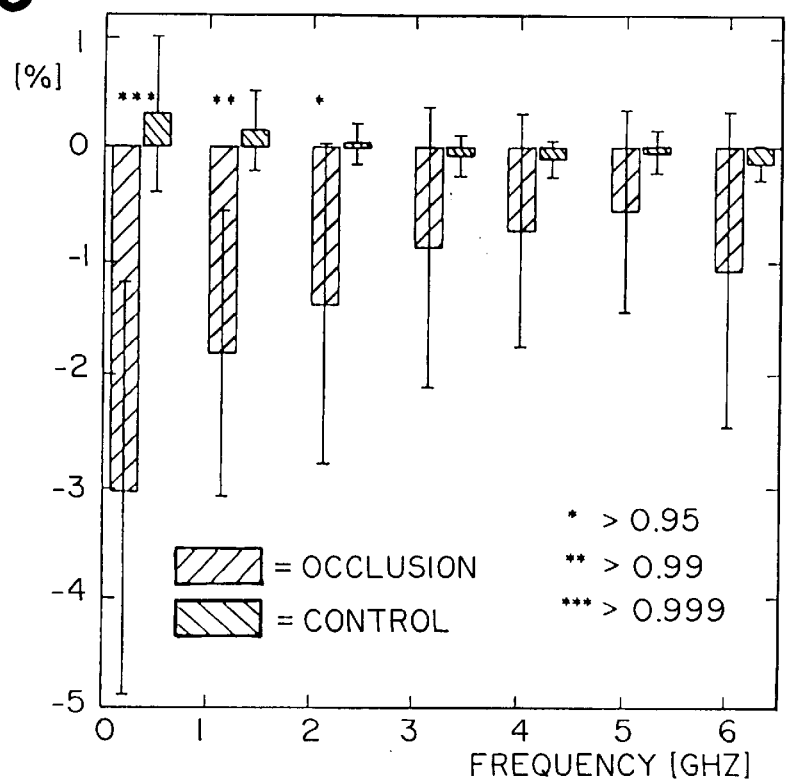

FIRST ITERATION (RYTOV APPROX.)

FIRST ITERATION (RYTOV APPROX.)

TENTH ITERATION

TENTH ITERATION

MATHEMATICAL MODEL (CONTRAST 10%)

MATHEMATICAL MODEL (CONTRAST 10%)

ELECTROMAGNETIC IMAGING AND THERAPEUTIC (EMIT) SYSTEMS

FIELD OF THE INVENTION

The present invention relates to EMIT systems. Specifically, the invention pertains to apparatus and method in which multi-frequency microwave in combination with preferably low frequency is structured to generate a multi-source externally focused microwave for tissue ablation. The invention includes several versions of EMIT systems differentiated on the basis of frequency levels and complexity. Further, the invention includes a computer implemented software specifically configured and tailored to the EMIT system with a graphical and three-dimensional tomographic imaging interface.

BACKGROUND OF THE INVENTION

Electromagnetic tomography is a relatively new technology with enormous potential for use in medical and related industries. Specifically, the technology is becoming prominently mature and practicable for use in internal, non-invasive, real-time imaging of the physiologic properties of tissues and organs, based on tissue dielectric properties differentiation.

Known microwave tomographic imaging utilizes microwave radiation to image an object by detecting the effects the object had on the microwave beam after it has encountered the object. The changes effected in the reflected microwave, due to this encounter, are dependent upon the dielectric permittivity and conductivity properties of the tissues of the object being imaged. Specifically, for a given microwave frequency, the observed changes in the reflected microwave echo signify a specific signature of the imaged tissue.

Microwaves are ultra-high to super-high frequency radio waves with very short wavelengths ranging from approximately 130 centimeters down to fractions of a millimeter. Frequencies range between 0.1 Giga Hertz (GHZ) to 3000 GHZ. The microwave range which is currently used for microwave imaging of biological tissues is in the range of about 0.5 to about 3 GHZ. However, other ranges of the microwave spectrum may also be used as well. The determinant in the selection of the range is that the radiation be non-ionizing to prevent destruction of tissue members or cells. Accordingly, there are biophysical parameters which should be considered when determining a compatible frequency range.

The prior art utilizes two basic categories of microwave imaging. The first category is static imaging based on forming images by determining the absolute permittivity values of the microwave radiation after its interaction with the object. The second category is dynamic imaging which is based on variations in permittivity within the object occurring at the time of incidence of the microwave radiation. The latter form of imaging is extremely useful in applications in imaging biological tissues to monitor ongoing physiological change. Both static and dynamic imaging techniques require an active imaging process whereby a microwave scanner employs moving or scanning incident radiation and detects the changes in the microwave radiation based on interaction with the object being imaged.

Using dynamic imaging, image reconstruction is based on the difference in diffracted fields recorded from several data sets taken from a body with a changing dielectric contrast. However, internal imaging within larger bodies poses resolution problems which limit the application and scope of dynamic imaging. The present invention provides significant advances over the prior art by integrating biophysical, computer software and microwave tomography technologies to provide a high resolution image.

SUMMARY OF THE INVENTION

The invention integrates and implements biophysical, algorithmic/computer and microwave tomography devices and methods to provide a three-dimensional tomographic system. Specifically, the invention includes a new method and system for medical physiological tomography wherein a one frequency three dimensional microwave tomographic system (3D MWT) is combined with a one frequency three dimensional electrical impedance tomographic system (3D EIT) capable of imaging a full scale biological object(s) such as a human torso.

Specifically, the present invention provides a non-invasive real time imaging of the physiologic properties and temporal changes of tissues and organs based on tissue dielectric properties differentiation. For example, using the invention it has been shown that the dielectric properties of the myocardium are sensitive indicators of its physiological condition, including local blood supply, ischemia and infarction. The degree of change in the myocardial dielectric properties provides adequate data for reconstruction using microwave tomography. More specifically, the invention includes an EMIT system with a number of microwave frequencies (microwave spectroscopy) and other frequencies lower than the particular cellular membrane relaxation frequency. This frequency composition of the invention enables estimation of biophysical parameters of the tissue as cellular volume fraction, intracellular and membrane resistivities, cell membrane capacitance, tissue free and bound water content and tissue temperature. It should be noted that such information is critical not only for cardiology but also for other branches of medicine, inter alia, oncology, urology, neurology and other studies.

Further, the present invention provides mathematical models and computer implemented algorithms for constructing heretofore unavailable quantitatively reconstructed clear structural images which depict exact distribution of dielectric properties within an object

DESCRIPTION OF THE PREFERRED EMBODIMENT

The present invention provides a three dimensional microwave tomographic system which is combined with a three dimensional electrical impedance tomographic system. Specifically, the invention includes a one frequency three dimensional microwave tomographic system combined with one frequency three dimensional electrical impedance tomographic system capable of imaging a full scale biological object(s) such as, for example, portions of a human torso. The disclosures of the present invention provide both theoretical and experimental values which show some of the advantages and advances of the invention relative to the physiological imaging prior art currently available in medical diagnosis and therapy.

The present invention contemplates a staged approach in which a first generation EMIT system is launched with possible upgrades to a second generation system. The first generation is distinguished in that it has two systems having the following characteristics (a) Multifrequency microwave spectroscopic tomographic 0.2–6 GHZ, and (b) single microwave frequency (about 0.8 to 1 GHZ) with a single low frequency (about 20 Hz to 200 kHZ). The second generation comprises of three systems with the following distinguishing characteristics: (a) Multifrequency microwave 0.2–6 GHZ, (b) One low frequency approximately 200 kHZ and c) multisource externally focused microwave for tissue ablation (60° C.).

Further, the present invention provides unique algorithm and software to enable the generation of very accurate images from the EMIT systems. Specifically, the algorithms enable image reconstruction from microwave tomography. Since the linear optics approximation used in X-ray tomographic image construction is not readily adaptable to microwave tomography primarily because of electromagnetic wave propagation through biological media involving diffraction and interference phenomenon, there is a need to develop specific algorithms to solve Maxwell equations or their scalar approximation. The present invention provides algorithmic models and software programs to solve these equations and enable a reconstruction of images as needed. Details of the types of models, assumptions, limitations and related mathematical postulations are discussed below. Several structures, features and alternate embodiments are disclosed herein to provide the inventors the protection they are deemed entitled. The invention is multi-faceted and may include several inventions and embodiments which applicants may pursue individually or combine as apparent. Further, it should be noted that experimental results and conclusions as provided herein are for example purposes only and should not be taken to unduly limit the present application in any way.

BRIEF DESCRIPTION OF THE DRAWINGS

FIG. 4 is a flow diagram of an alternate reconstruction algorithm for the reverse problem solution.

FIG. 5 is a graph of canine cardiac tissue dielectric characteristics as a function of heart cycle.

FIG. 6 is a graph of canine cardiac tissue dielectric characteristics as a function of heart cycle.

FIG. 15 is a graph of blood oxygen contents correlated to first order dielectric correlation coefficients and frequency of microwave emissions.

FIG. 16 is a graph of blood oxygen contents correlated to second order dielectric correlation coefficients and frequency of microwave emissions.

FIG. 28 is a chart of relative changes of E' during acute infarction.

FIG. 29 is a chart of relative changes of E" during acute infarction.

DETAILED DESCRIPTION OF THE INVENTION

1. Background of Microwave Tomographic Spectroscopy

Figure 1:
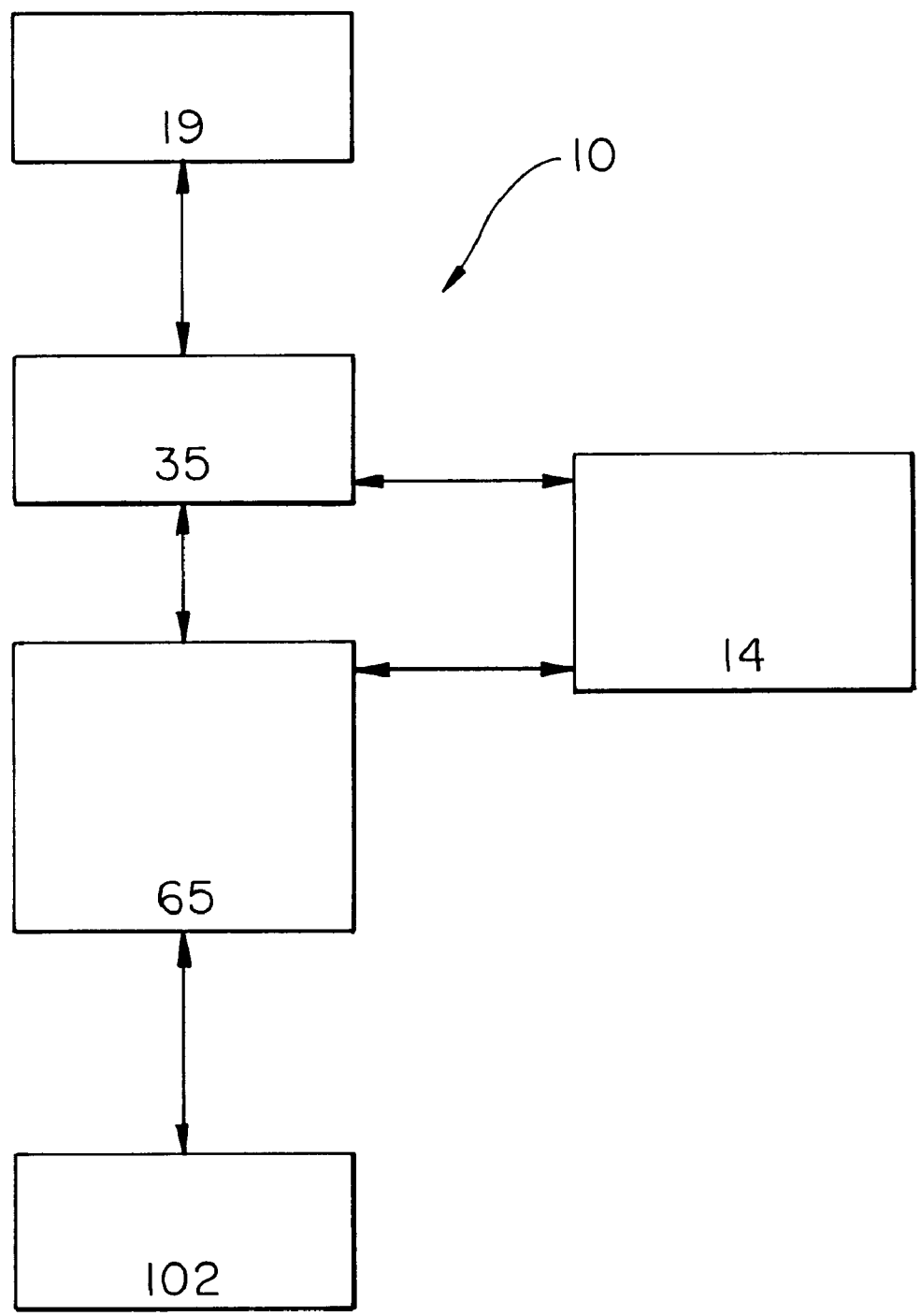
FIG. 1 is a schematic diagram of the tomographic spectroscopy system of the invention.

Microwave tomographic imaging uses microwave radiation to image an object by detecting the effects the object had on the microwave beam after it has interacted with the object. With microwave radiation, it is the dielectric permittivity and conductivity properties of the tissues of the object being imaged that determines the nature of the interaction. The dielectric permittivity and conductivity properties of an object are expressed together as a complex permittivity.

Microwaves, as a component of the electromagnetic radiation spectrum, are in the frequency range between approximately 0.1 Giga Hertz GHz to 300 GHz. This corresponds to the wavelength range between 300 mm and 1 mm. The microwave range useful for microwave imaging of biological tissues is in the range from about 0.5 to about 3 GHz, but other ranges of the microwave spectrum can be used as well. The quantum energy of the photons in this range of the electromagnetic spectrum comprises non-ionizing radiation.

In general, microwave imaging differs from X-rays, positron emission, ultrasound, or nuclear magnetic resonance imaging because the microwave radiation interacts with the object to be imaged as a function of the complex permittivity of the object. Complex permittivity is made up of the dielectric permittivity and the dielectric loss. The dielectric permittivity is the real part and is given by the equation:

$$E' = e/e0 \qquad \text{Equation 1.}$$

The relative dielectric loss is given by the imaginary part as $$E'' = \sigma/2 \, \pi f E_0 \qquad \text{Equation 2.}$$

Where $E_0$ is the dielectric permittivity of vacuum, s is the conductivity of the material and f is the working frequency. For example, water has a fairly broadband dielectric permittivity, being approximately 80 at about 1 GHz and falling to about 4.5 at frequencies higher than 100 GHz. Water dielectric loss increases from values at about 1 GHz to around 25 GHz. An additional factor affecting the permittivity of water is its temperature.

There are two basic categories of microwave imaging. The first category is static imaging based on forming images by determining the absolute permittivity values of the microwave radiation after its interaction with the object. The second category is dynamic imaging which is based on variations in permittivity within the object occurring at the time of incidence of the microwave radiation. This second form of imaging is extremely useful in applications for imaging biological tissues to monitor ongoing physiologic change. It must be understood, however, that both static imaging and dynamic imaging still require an active imaging process whereby a microwave scanner employs moving or scanning incident radiation and detects the changes in the microwave radiation based on interaction with the object being imaged.

Most non-biological objects that are amenable to imaging by microwaves are very simple structures in terms of dielectric and conductivity variability. On the other hand, biological tissues demonstrate a wide range of relative dielectric constants. These ranges are thought to be due in large part to the interaction of the microwave radiation with charges on the surface of cellular membranes, the actual structure of the cellular membrane with its hydrophobic layer between the hydrophilic layers, and the water and electrolyte content both within and without the cellular structures. Consequently, biological tissue interaction is extremely complex and will even change with time due to the subtle change in temperature secondary to the absorption of the microwave energy used to obtain the microwave image. This absorption is converted to heat, especially by water. This is quite important because the average biological tissue contains approximately 70% water.

Tomographic microwave imaging has used a series of microwave emitters and receivers arrayed spatially around an object to be imaged. In a 1990 publication in IEEE Transactions on Biomedical Engineering, vol. 37 no. 3; pp. 303–12, March, 1990, titled "Medical Imaging with a Microwave Tomographic Scanner", Jofre et al., disclose a cylindrical array of microwave emitters and receivers. The array totaled 64 waveguide antennas in four groups of 16 antennas. Each waveguide antenna is capable of function as an emitter or receiver. The object to be imaged is placed within the array circle and immersed in water to minimize attenuation of the microwave incident beam as it interacts with the surface of the object Each antenna within a group emits in sequence and the 16 antennas in the group opposite the emitting group act as receivers. This procedure is sequentially repeated for each antenna until one revolution is completed. The output microwave signal was 2.45 GHz, providing a collimated field approximately 2 cm in height and having a power density of less than 0.1 milliwatt per square centimeter at the object The Jofre et. al structure uses a coherent phase quadrature detector to measure the magnitude and phase of the signal from the receiving antennas. The data is digitized and a computer performs a reconstruction of the image based on changes in the microwave radiation. This reconstruction is carried out by an algorithm formulated to yield an approximation of the microwave diffraction in two dimensions. The algorithm makes use of the Born approximation which assumes that scattering acts as a small perturbation on the illumination and therefore the field within the body is approximated by the incident field. This approximation problem remains as a substantial limitation to microwave tomography.

In a publication in Journal of Neuroscience Methods, 36; pp. 239–51, 1991, entitled "Active Microwave Computed Brain Tomography: The Response to a Challenge", Amirall et al., disclose an application of the cylindrical array in JofrE's paper to imaging the brain. The image was again reconstructed using a diffraction algorithm for cylindrical geometries using Fast Fourier Transform techniques and the Born first order approximation. The data as reconstructed through the algorithm generates a contrast in permittivity values of a cut of the body as a function of the spatial coordinates of the portion of the imaged body creating that contrast in permittivity. Resolving power theoretically is limited to diffraction values of one half the wavelength of the microwave radiation. For a frequency of 2.45 GHz this would mean a theoretical minimum resolution of about 6 cm in air and 7 mm in water. As a consequence of the reconstruction algorithms and limitations in the electronics used in the devices, these theoretical values are not achieved.

The validity of the first order approximations and the algorithms used in the above device limit imaging to static images of small bodies such as limbs. In the case of larger bodies, such as a human head, the reconstructed image would only show correctly the outer contour of the body but not the internal structure.

Using dynamic imaging, image reconstruction is based on the difference in diffracted fields recorded from several data sets taken from a body with a changing dielectric contrast. Amirall et al., were able to achieve internal imaging within the larger bodies, however, resolution was approximately only half the theoretical predictions.

Figure 2:
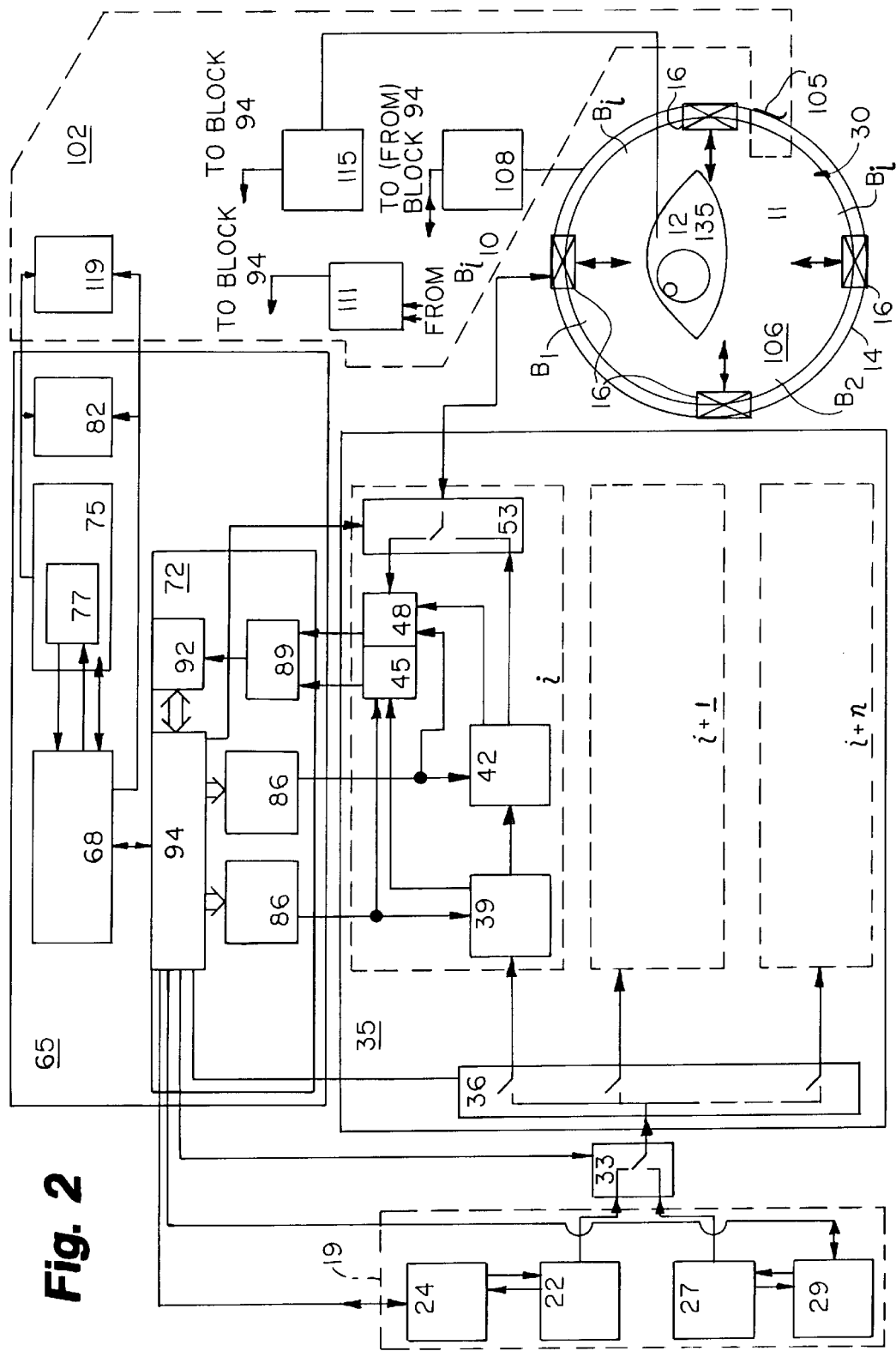
FIG. 2 is a schematic diagram of the tomographic spectroscopy system of the invention.

FIGS. 1 and 2 are each schematic diagrams of a tomographic spectroscopy system 10 of this invention. Utility of this invention encompasses many fields, however the preferred field described below is that of medical uses. More particularly, the embodiments of the invention claimed below relate to non-invasive diagnosis and therapy for heart arrhythmias. The system enables rapid and highly accurate non-invasive detection and localization of cardiac arrhythmogenic foci, as well as non-invasive cardiac mapping capabilities. System 10 accomplishes these procedures using a multiple frequency regimen, signal encoding techniques, improved mathematical algorithms, and previously unrecognized correlation functions. These and other features of the invention will become apparent from the more detailed description below.

Identification of the origin of cardiac arrhythmias has previously depended on one of three principal techniques: catheter mapping, electrical excitation mapping during cardiac surgery, or body surface mapping of electric potentials or magnetic fields. Each of these techniques has substantial risks and limitations. For example, catheter mapping and excitation mapping during surgery are inherently invasive, access limited, and time sensitive. Body surface mapping can be performed in a non-invasive, low risk manner but with such poor definition that the data is generally considered unsuitable for directing therapy. The mapping may be performed using either sequential temporal changes in the electrical potential of the body or sequential changes in magnetic fields on the body surface.

The invention does not require insertion of a catheter into a body, nor does it require inserting probes into cardiac tissue. However, reliable and precise (<about 5 mm) three dimensional reconstruction of the heart and its electrical excitation sequence is now possible using this invention. Use of the techniques listed below for ablation of arrhythmogenic sites is non-invasive and advantageously utilizes the different frequencies and directions of energy available so that the ablation threshold will occur only at the designated location. The invention does anticipate invasive procedures, for example, ablation systems delivered by catheters or surgical procedures to accomplish physician directed therapy.

As briefly mentioned above, the invention utilizes novel correlation functions. These functions relate to tissue physical properties and changes of those properties during cell excitation. In particular, the dielectrical behavior of biological tissue can be defined by two characteristic parameters: dielectric permeability and conductivity. The parameter functions include frequency, temperature, and tissue type. The tissue type parameter provides opportunities for detection of anatomical structure by measuring transmitted, i.e. reflected and scattered, electromagnetic energy through tissue. For homogenous objects the dielectric characteristics can be readily detected by measuring amplitude and phase of transmitted electromagnetic radiation. However, the problem is more complicated when trying to measure the dielectric values of radiation transmitted through non-homogenous biological tissue simply by using measured amplitude and phase of the transmitted wave. This problem is known as the "inverse" or "reverse" problem and has attracted some attention to its solution. This invention incorporates the strong dependence of tissue characteristics on temperature, and solves the "reverse" problem in novel ways by using multiple frequency and multiple position emitter-receiver configurations.

Referring to FIGS. 1 and 2, system 10 comprises emitter-receiver subassembly 14 suitable for mounting a plurality of microwave emitters-receivers 16. A preferred configuration of emitters-receivers is in a circular array. However, any other 3-Dimensional or 2-Dimensional array configurations, suitable for certain parts of the body or for the whole body (for example, the "head," "heart," "arm," "leg," etc.), is usable in this invention. Each emitter-receiver 16 may be enabled for radial movement relative to the circular array.— Sub-assembly 14 may also comprise a plurality of vertically stacked emitters-receivers. A power source 19 provides narrow pulse-width electromagnetic energy signals to each emitter of not more than about 10 mW/cm2 incident power density on an object. Preferably, the frequency band width of these narrow pulse-width signals is centered between about 0.1 GHz to about 6 GHz, and more preferably within the frequency range of about 0.2 GHz to about 2.5 GHz. It is recognized however, that this system may be combined with a low frequency source (from about 20 Hz to about 2 MHz) to provide the electromagnetic impedance tomographic subsystem of an improved imaging device having a multi-source input block, discussed further below. Power source 19 may comprise either a plurality of power sources or a single power source, such as a generator. In the embodiment of FIG. 2, power source 19 comprises a sweeping diagnostic generator 22, a diagnostic generator control block 24, an ablation generator 27, and an ablation generator control block 29. Sweeping diagnostic generator 22 provides multiple frequency low power energy for use in diagnostic applications, while ablation generator 27 provides high power energy for microwave ablation of designated tissue regions. Selection of either of the above generators is accomplished by switch 33 which connects generator output with the emitters 16.

A channelization mechanism 35 is provided for activation and control of channels i, i+1, i+n, for energy emission and reception. This subsystem comprises a channel number switch 36, an amplitude attenuator-detector manipulation (ADM) 39, a phase rotator-detector 42, an amplitude detector 45, a phase detector 48, and an antenna mode switch 53. In diagnostic operation, channel number switch 36 connects the output of the diagnostic generator 22 with the input of the emitter (or a multiple of emitters) at any particular time. In the ablation or therapeutic mode, the switch connects all channels with the output of the ablation generator 27. Amplitude attenuator-detector 39 and phase rotator-detector 42 are in the emitter path of all channels. Amplitude attenuator-detector 39 attenuates the amplitude of emitted power, and with phase rotator-detector 42 detects and encodes the output signal. Amplitude detector 45 and phase detector 48 are in the received path of all channels and, in the diagnostic mode, detect and decode the amplitude and phase of the received signal. It is recognized that other coding means, such as polarity, may require additional encoding/de-coding components. Antenna mode switch 53 functions in all channels to connect the output of the emitter path with the antenna or input path, at the receiver path, with the same antenna.

Computation and control module means 65 includes a central processing unit (CPU) 68, an interface subsystem 72, a display 75 and a display software 77, as well as a memory 82. The interface subsystem 72 consists of a digital-to-analog converter(s) (DAC) 86, a multiplexer 89, an analogto-digital converter (ADC) 92, and a control block 94 which creates time synchronization of controlled processes and receives data to be analyzed.

An auxiliaries subsystem 102 comprises a thermostatic shield 105 for controlling the temperature of an interface medium 106. A suitable interface medium, for example, would be a fluid such as a solution of titanium and barium. Other suitable liquids (or substrates), such as specially homogenized fatty solutions, are usable in this invention. These liquids would have a preliminary dielectrically adjustable dielectric permittivity between about 50 and 90 at 2.45 GHz and a dielectric loss between about 5 and 25, between the emitters-receivers 16; the subsystem 102 also comprises a thermostatic control block 108 for controlling thermostatic shield 105, and a basic channel control block 111 for control of the received signal from the Bi control channels when the system 10 is in a calibration mode. Additional auxiliary components may be added depending on desired performance features of the system, for example, an electrocardiogram analyzer and/or a printer 119 may be useful to the system 10.

Figure 3:
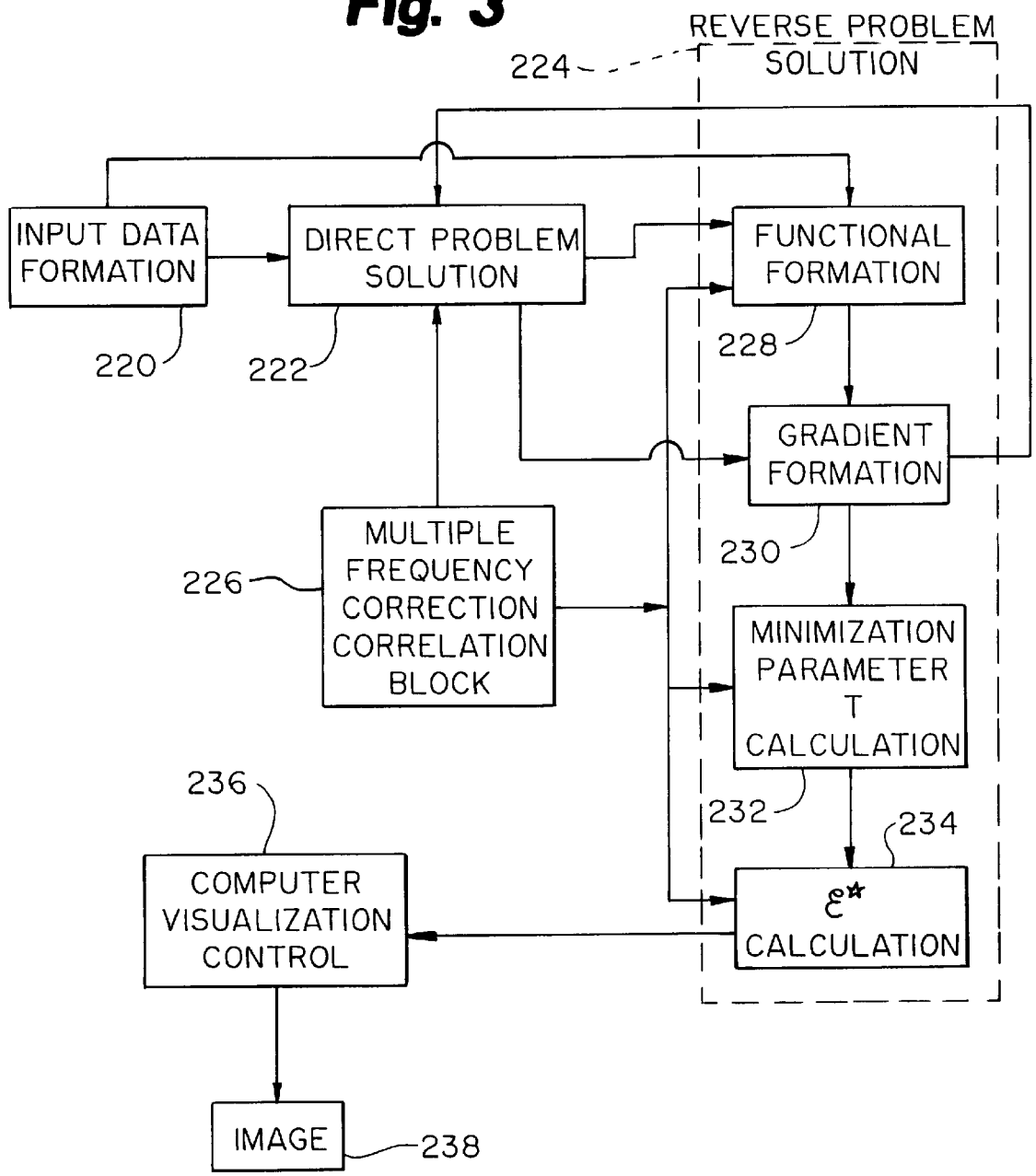
FIG. 3 is a flow diagram of the algorithm for the reverse problem solution.

In a sequential multiple frequency tomographic spectroscopy system 10, target tissue 135 is irradiated in sequence with low energy microwave radiation from the first to the nth emitter (receiver) 16, while simultaneously taking measurement of the received signals in (emitter) receivers 16 which in that particular step of the sequence are not functioning as an emitter. Several emitter-receivers 16 are used to receive signals emitted by a single emitter-receiver 16 in any given instance of time. The system 10 rapidly changes channel number and antenna mode in sequence according to the above configuration. After one cycle of n-channel emissions and receptions, sweeping diagnostic generator 22 provides another cycle of n-channel switched measurements. The total quantity of cycle measurements is normally not more than N×M, where N is the quantity of antennas, and M is the quantity of used diagnostic frequencies. It is also recognized that simultaneous measurements may be obtained using a multiple encoded frequency configuration. Following the measurements, system 10 solves the "reverse" problem according to the received information and the novel algorithms described more fully below in relation to FIGS. 3 and 4. When measuring physiologic changes it is important to understand the time it takes for a physiologic event to occur, for example a myocardial contraction. These time periods are defined as tissue event time cycles.

Data acquisition in system 10 is performed in time intervals which are a fraction of a tissue event time cycle so that data acquisition may occur many times during each tissue event and are stored in memory 82. Reconstruction time is fast enough that body motion is not a problem. Anatomical object structure and temperature profiles are observable on display 75, may be manipulated using routines of display software 77, and may be printed using printer 119. The arrhythmogenic zones of the heart are defined as those regions with particular E' and e" values. Spatial coordinates of these zones are defined with the help of the display software, the CPU, and the memory.

During measurement cycles, system 10 periodically makes temperature control corrections of the interface medium 106 with the aide of the thermostatic control block 108. System 10 also synchronizes with the heart cycle in which the tissue is resident using electrocardiogram analyzer 115.

A key feature of system 10 which facilitates the speed and accuracy of calculation is the use of a coding device for encoding the microwave signals supplied to the emitters. When the receivers receive the corresponding signals after interaction with the tissue, the signals are distinguishable by their originating emitter or emitter group. Preferred encoding techniques are phase, amplitude, or polarity modulation; however it is also within the scope of the invention to employ frequency modulation. Frequency modulation may be useful in certain applications where simultaneous emissions from a plurality of emitters are required.

System 10 is one embodiment for using the novel method steps of this invention which permits non-invasive tomographic spectroscopy of tissue. The method comprises the steps of: providing a radiation power source; providing a plurality of radiation emitter-receivers; and controlling the plurality of radiation emitter-receivers so that a plurality of emitter-receivers are able to emit multiple frequency radiation from the power source to a plurality of emitter-receivers that are receiving the radiation. Further steps include: placing an interface medium between the emitting and receiving emitter-receivers for dielectric matching; placing tissue to be irradiated within the interface medium; emitting the radiation from the emitter-receivers; receiving the radiation in the emitter-receivers after interacting with the tissue; and measuring a change in the radiation after interacting with the tissue.

As disclosed above, novel algorithms are used to solve the "reverse" problem calculations. In this invention, there are no approximations, such as the Born approximation discussed above, used to define dielectric or conductivity parameters of non-homogenous irradiated tissue objects. Rather, the measuring step of the above method incorporates both old and new concepts to refine and render useful the data derived from this form of electromagnetic imaging. In particular, and as shown in the flow diagram of FIG. 3, the measuring steps comprise computations using an input data formation component 220, a direct problem solution component 222, a reverse problem solution component 224, a multiple frequency correlation component 226, a computer visualization control 236, and a tomographic spectroscopic image 238.

The direct problem solution is a known calculation which solves microwave propagation from emitter to receiver through a biological means. Solution of the reverse problem allows precise computation and generation of a tomographic spectroscopically useful image of the tissue based on the measured change of the microwave radiation. The reverse problem solution steps comprise: determination of a functional formation component 228 which sums the input from all emitters-receivers; using a gradient formation component 230 as a derivative of the functional formation component to simplify processing speed; calculating a minimization parameter tau to verify the accuracy of the gradient function and to reconstruct in the most accurate manner; and performing an E* calculation 234. The E* calculation 234 uses the following:

$$e^* = E' + ie'' \qquad \text{Equation 3}$$

Where E' said e" are the values of dielectric permittivity and loss measured by the invention and i represents the imaginary number. Using e* as a representative value of E' and e" is a convenient mathematical tool. It should be understood that the invention may also use either E' and/or e" as the measured dielectric parameter for generating an image. The reason for using e* is that dielectric contrast between tissue and/or tissue physiologic states may be found in either a difference or change in E' and/or e". If E' and e" are calculated together as e* then any dielectric change in either E' or e" will be detected in an e* calculation. As will be seen later, some physiological dielectric changes are best evaluated by using only E' or e". It is important to recognize that wherever e* is used, E' or e" can also be used in place of e*.

The flow chart depicted in FIG. 4 represents an embodiment of the present invention which can be used in a catheter system as well. Data is fed into a direct problem solution step 240 from a working arrays formation step 242 and an antenna simulation step 244. The working arrays formation step 242 receives data from a frequency and temperature correlation step 248 which derived its initial values from a zero approximation step 250. The antenna simulation step 244 provides values for starting the calculation process acting as a base line from which to construct an image. Direct problem solution step 240 then is able to solve an image problem based on knowing what the amplitude and phase of the emitted microwave energy is and making an assumption as to what the biological tissue dielectric effects will be and calculating an expected amplitude and phase value for the transmitted microwave energy. This solution from the direct problem solution step 240 is then passed to reverse problem solution step 252 comprising an equation system formation step 254, a Jacobian formation step 256, and a matrix irreversing step 258. The reverse problem solution step 252 then calculates an image of the biological tissue based on known emitted microwave and other amplitude and phase values and known received amplitude and phase values from the emitter receiver arrays. In effect, the reverse problem solution is generating the tomographic image by knowing the amplitude and phase of the emitted energy and the amplitude and phase of the transmitted or received energy in order to calculate the dielectric characteristics of the biological tissue through which the energy has passed. This image data from the matrix irreversing step 258 is then passed through an error correcting iteration process involving an error estimation step 260 and a first error correction step 262. For each value of amplitude and phase emitted and received, where i is equal to 1–n, the matrix irreversing step 258 in conjunction with error estimation 260 and first error correction 262 forms an iterative loop that begins with inputting the first grid point $e^*\_T$ into the error estimation step 260. For each value of i, from 1–n, a $e^*j+1$, $Tj+1$ is generated in which j is the grid number in the coordinate system for generating the two or three dimensional image construct and where j is equal to values from 1–n. After each $e^*$, T value has undergone an error estimation and first error correction, the value is then passed to an anatomical and T reconstruction and anatomy error estimation step 264. At this point the value as fed into error estimation step 264 is compared with the e" value and if the error estimation has occurred the value is passed onto an anatomical structure and T visualization step 266 which serves the purpose of generating the two dimensional or three dimensional image of the biological tissue based on dielectric contrast. If, however, the error estimation step results in a no response, a data point is passed to a second error correction step 268 which then adjusts, in conjunction with the first correction step 262, the values generated by frequency and temperature correlation step 248.

FIG. 5 is a graph demonstrating the capability of system 10 to detect cardiac excitation by changes in dielectric characteristics of cardiac tissue. In particular, FIG. 5 shows the change in E' values at the onset and throughout the period T1 of an electrical excitation process and during the transition period T2 to recovery. FIG. 6 discloses similar detection capabilities for system 10, but for values of the E" dielectric parameter. In both FIGS. 5 and 6, each point represents a mean value for seven measurements.

Figure 7:
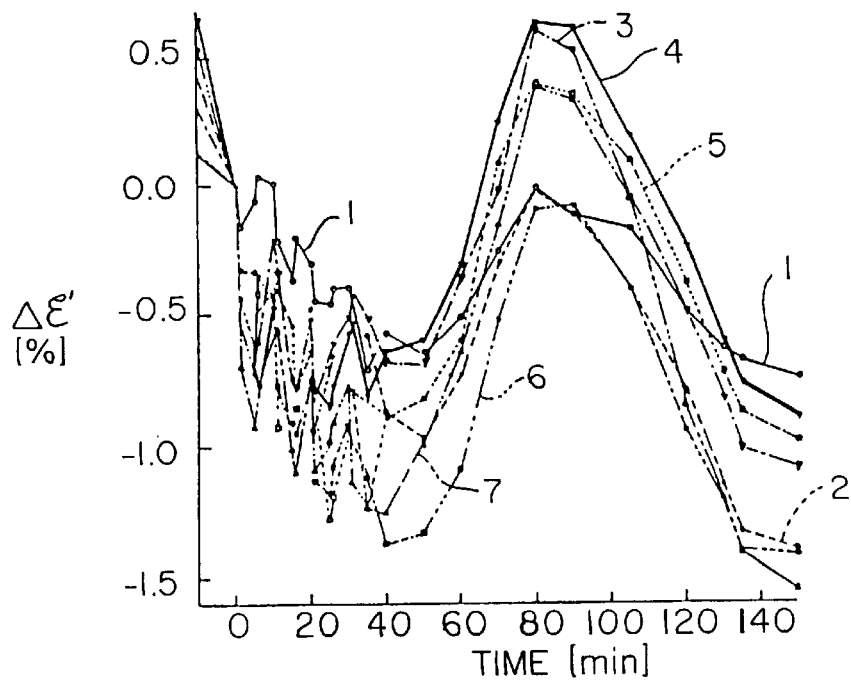
FIG. 7 is a graph of canine cardiac tissue dielectric characteristics as a function of occlusion and re-perfusion.
Figure 8:
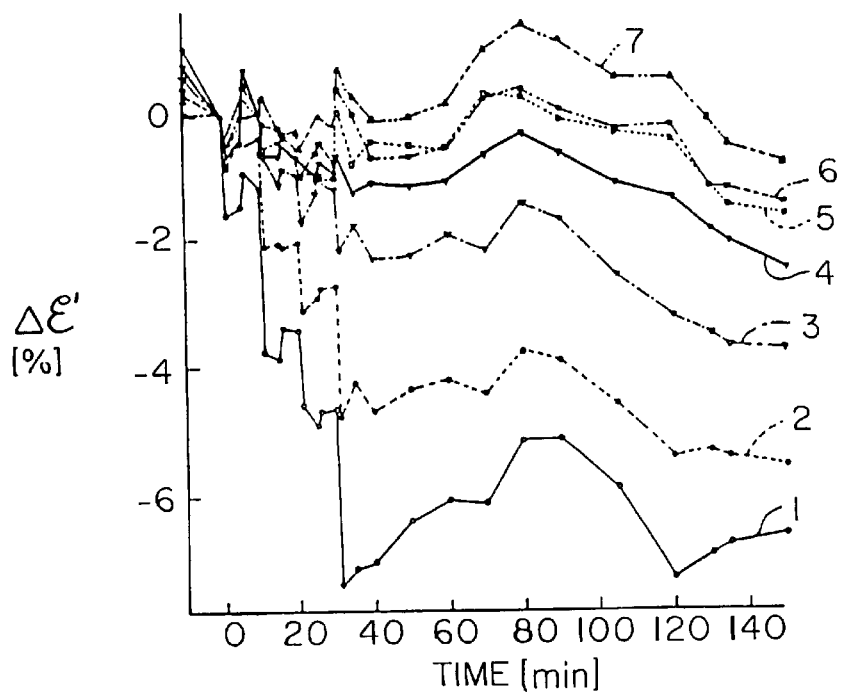
FIG. 8 is a graph of canine cardiac tissue dielectric characteristics as a function of occlusion and re-perfusion.
Figure 9:
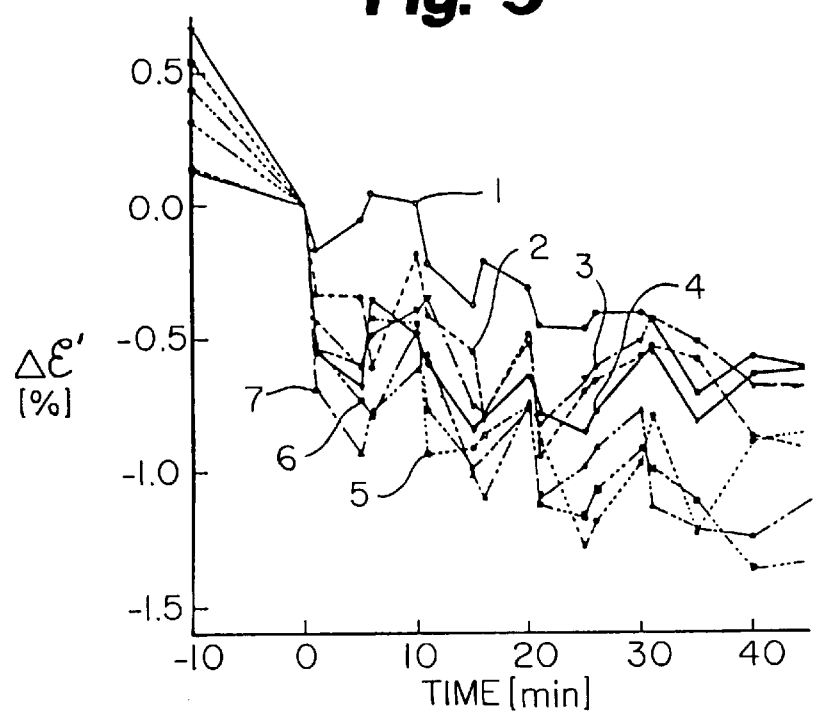
FIG. 9 is a graph of canine cardiac tissue dielectric characteristics as a function of occlusion and re-perfusion.
Figure 10:
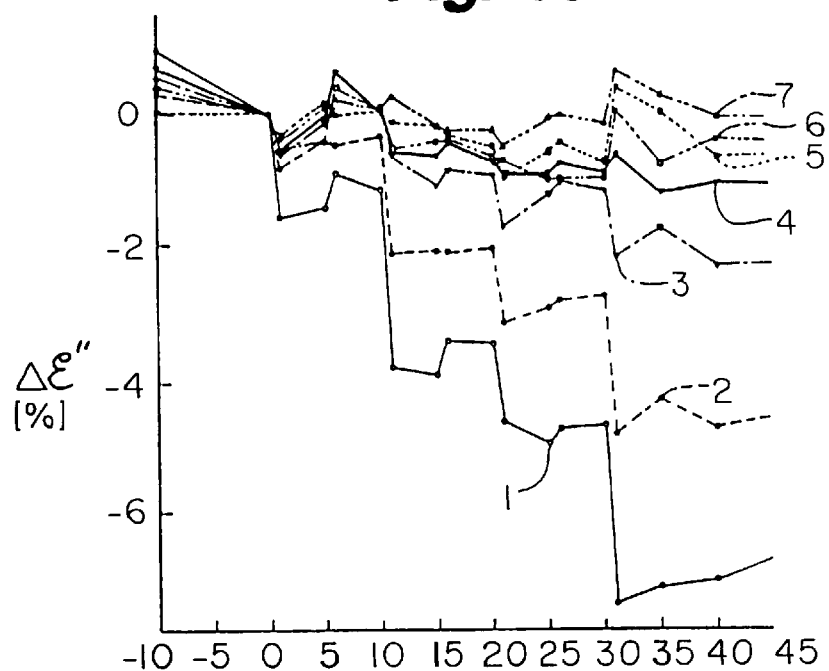
FIG. 10 is a graph of canine cardiac tissue dielectric characteristics as a function of occlusion and re-perfusion.

FIGS. 7–10 are graphs demonstrating the percent change of a selected dielectric characteristic, for multiple frequencies, during a series of coronary arterial occlusions. FIGS. 7 and 8 disclose, over a long duration, a series of short occlusions followed by a long occlusion. These figures demonstrate the correlation of dielectric characteristics for E' and E" depending on the degree of cardiac ischemia. This pattern of dielectric changes conforms with the known tissue phenomenon of a protective effect from pre-conditioning prior to a total occlusion. FIGS. 9 and 10 disclose, over a short duration, a series of short occlusions followed by a long occlusion. These figures support the conclusions stated above in relation to FIGS. 7 and 8.

Figure 11:
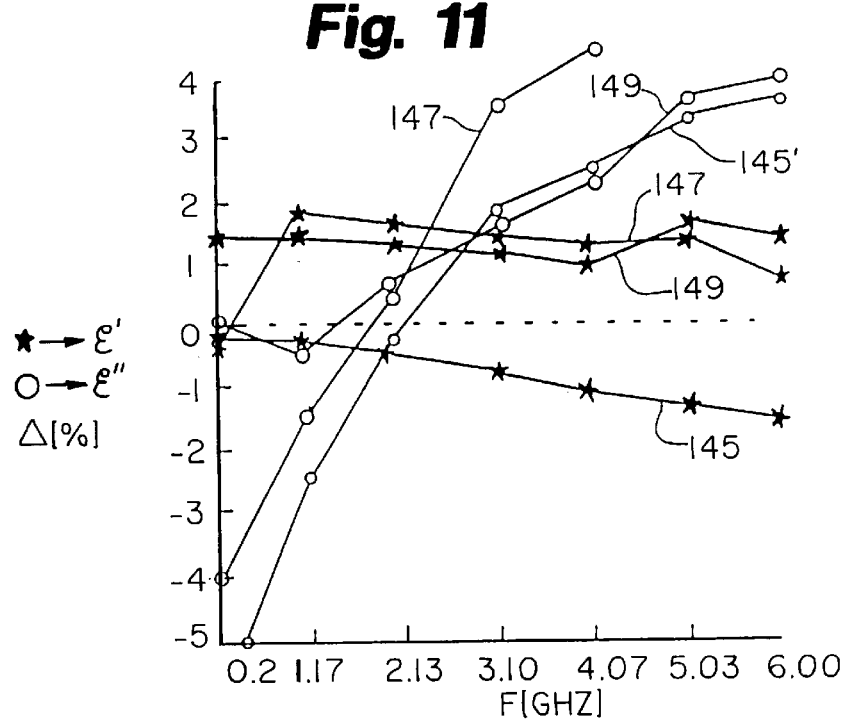
FIG. 11 is a graph of canine cardiac tissue first order and second order dielectric characteristics as a function of time and frequency of microwave emission.
Figure 12:
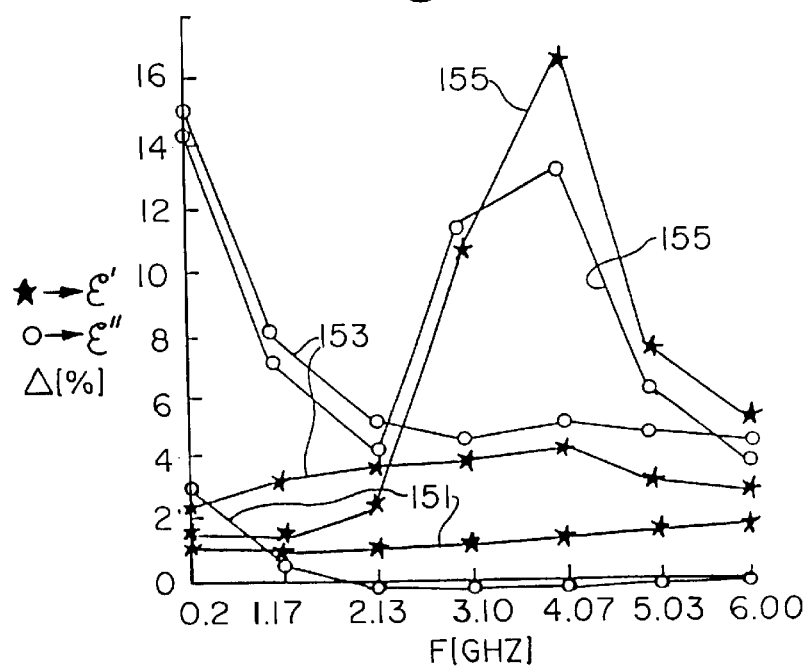
FIG. 12 is a graph of canine cardiac tissue first order and second order dielectric characteristics as a function of time and frequency of microwave emission.

FIG. 10 provides further example of the value of multiple frequency or spectroscopic analysis of tissue. In this figure, the curve of the values of percent change of E" at 4.1 GHz is relatively flat and less useful as compared to the corresponding values at either 0.2 GHz or 1.17 GHz. This highlights the need for system 10 to detect tissue excitation phenomena and other physiological events, e.g. ischemia, using multiple frequency techniques which might otherwise remain undetected or not useful in a single frequency analysis. This is further demonstrated in the $e^*(f)$ graphs of FIGS. 11 and 12, in which curves 145, 147, 149, 151, 153, and 155 represent time after occlusion (i.e., acute ischemia) of 0, 15, 30, 45, 120, and 125 minutes respectively for E' (shown by * curves) and E" (shown by o curves). The value of is $e^*/e^*$ before. Reperfusion occurs at time 125 minutes, and is represented by curves 155. These figures demonstrate that if analysis is limited to a single frequency, then very little useful data is derived during short tissue excitation periods. However, if multiple frequency analysis is conducted essentially simultaneously then the tissue physiological phenomena are clearly exhibited.

Figure 13:
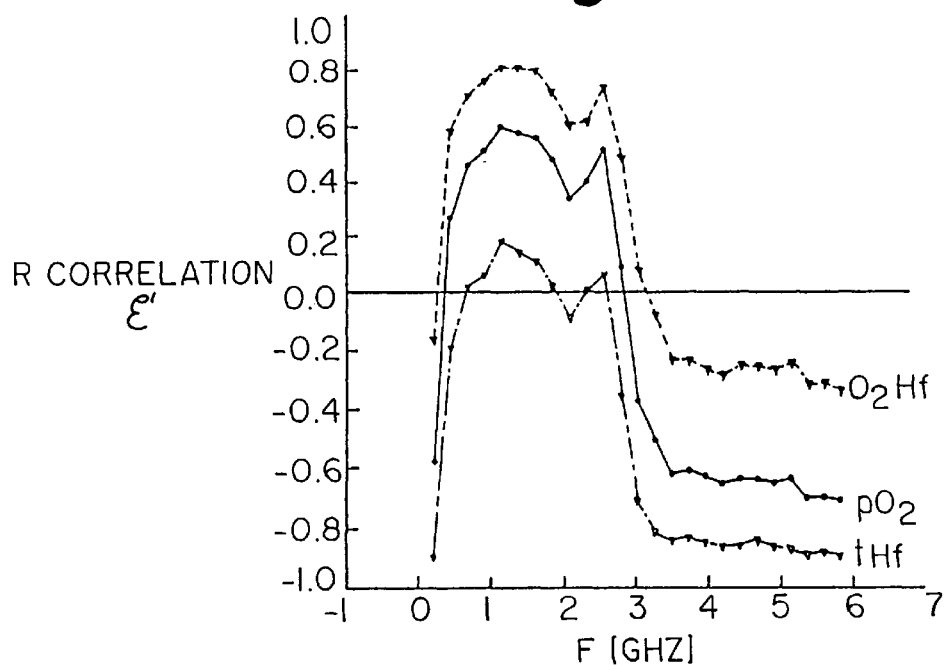
FIG. 13 is a graph of first order canine cardiac tissue dielectric characteristics correlated to frequency of microwave emission.
Figure 14:
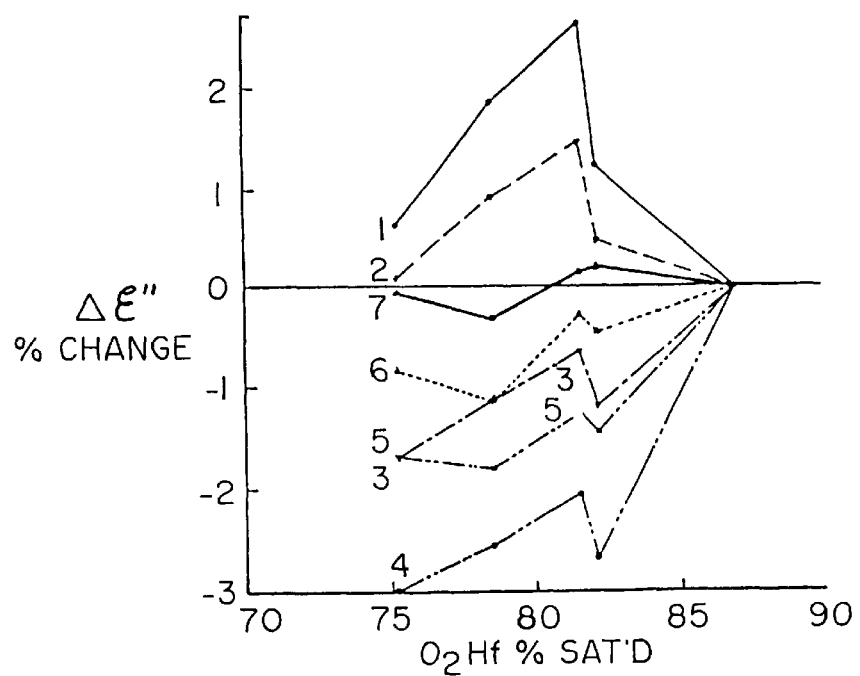
FIG. 14 is a graph of blood oxygen content correlated to second order canine cardiac tissue dielectric characteristics and frequency of microwave emissions.

FIGS. 13 and 14 disclose the correlation of dielectric characteristics to blood oxyhemoglobin content. In FIG. 13, the dielectric characteristic is the percent of (E'(HbO2)-E'(86.9))/E'(86.9), and in FIG. 14 the dielectric characteristic is the percent of (E"(HbO2)-E"(86.9))/E"(86.9). In each figure the frequency curves 161, 163, 165, 167, 169, 171, and 173 correspond to 0.2 GHz, 1.14 GHz, 2.13 GHz, 3.12 GHz, 4.01 GHz, 5.0 GHz, and 6.0 GHz, respectively.

The dielectric permittivity of oxyhemoglobin (HbO2), the partial pressure of oxygen (PO2) and total hemoglobin (tHb) content are correlated to microwave frequency range 0.2–6 MHz in FIG. 15. The highest degree of correlation for oxyhemoglobin occurs between the frequency range 0.5–2.5 MHz. Through this range the dielectric permittivity value e.

The correlation coefficient curve for E", dielectric loss, is disclosed in FIG. 16. The correlation coefficient for HbO2 is highest at approximately 2 GHz with the correlation coefficient for PO2 approaching unity between 2.5 and 4 GHz.

The correlation coefficient studies disclosed in FIGS. 15 and 16 are representative of the invention's ability to distinguish between oxyhemoglobin (HbO2) saturation percentage and PO2. Both of these values are important pieces of information useful to health care providers. Presently, there exists real time bed side photometric means for determining oxyhemoglobin saturation percentage called an oximeter. However, in order to obtain a PO2 value, arterial blood must be withdrawn from a patient into specialized syringes and put through a machine capable of directly measuring the partial pressure of gases in a liquid.

Figure 17:
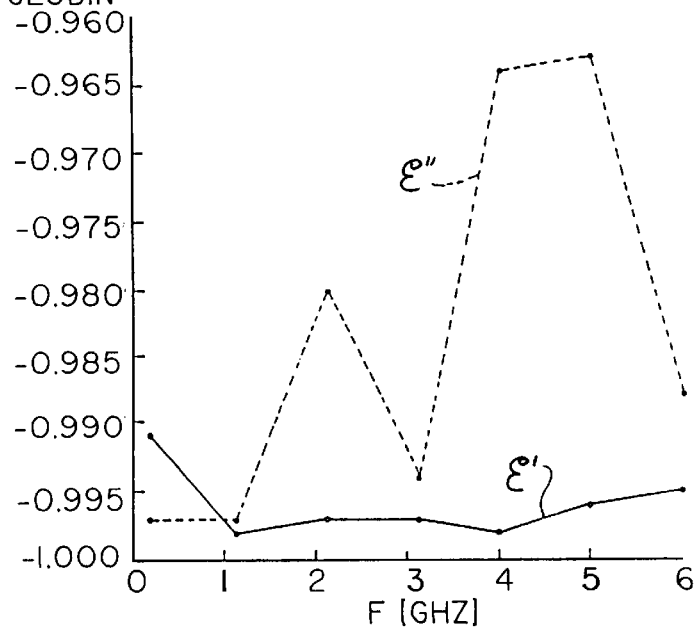
FIG. 17 is a graph of first order and second order dielectric coefficients correlated to total hemoglobin correlation coefficients and frequency of microwave emissions.

The E' and E" curves for total hemoglobin as a reference correlation are depicted in FIG. 17. The E' curve as shown is a fairly flat correlation curve that is fairly non-correlative, maintaining values of correlation less than −0.995 throughout most of the curve. The E" curve, however, shows an increase in correlation to total hemoglobin for the microwave frequency range between 4 and 5 GHz. As noted above in the discussions pertaining to FIGS. 3 and 4, correlation values for oxyhemoglobin PO2 and total hemoglobin may accurately derive from these correlation curves during a single frequency range scan from 0.2–6 GHz and calculating the dielectric permittivity E' and dielectric loss E" values for blood. The concentration of oxyhemoglobin saturation would then be best correlated with the E' value at, or about, 1.5 GHz, the PO2 value would then be calculated from the correlation value of the dielectric loss, E", calculated at, or about, 3.5 GHz, and tHb could be calculated from the correlation value of the dielectric loss curve, E", calculated at, or about, 4.5 GHz. Each scan through the frequency range from 0.2–6 GHz would require no more than several milliseconds of microwave exposure and then computing the value calculations. Thus, the present invention could feasibly be used at the bedside for virtual real time assessment of these parameters.

The present invention is able to provide a real time bedside monitoring of HbO2 saturation percentage and PO2 values. The present invention does so without necessitating removal of blood from the patient and the delay and cost of sending the blood to the laboratory for analysis.

This invention is not limited to HbO2 and PO2 values. Any blood and tissue component possessing a dielectric contrast characteristic is capable of direct measurement and real time evaluation, non-invasively, using this invention. The present invention also possesses an ability to detect dielectric characteristic changes that occur in a tissue that is becoming diseased. By way of example, a weakened diseased aneurysmal portion of a ten year old male's left ventricle was repaired. During this repair the diseased portion was resected from the heart such that the diseased portion was removed entirely. This requires that the resection margins contain normal myocardium. The invention was used to evaluate this piece of resected heart tissue and the test results are presented in FIGS. 18–20.

Figure 18:
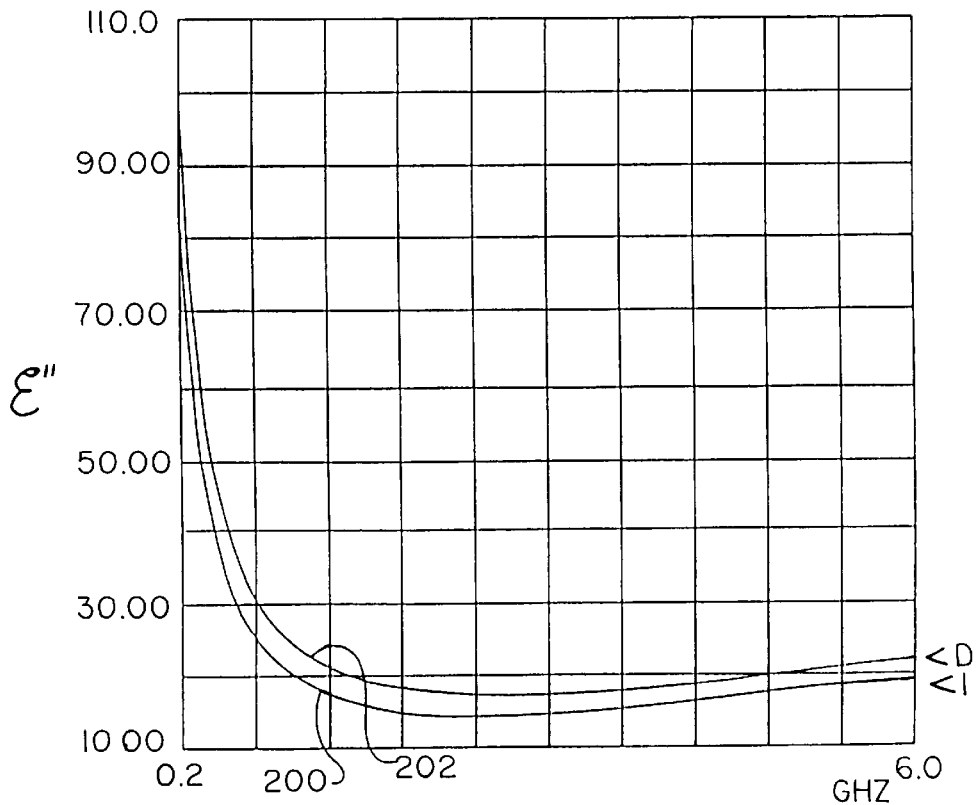
FIG. 18 is a graph of second order dielectric characteristics for a human left ventricular myocardium normal tissue to diseased tissue correlated by frequency of microwave emissions.

The E" dielectric loss characteristic of normal myocardium is shown in FIG. 18 as a curve 200 measured over a microwave frequency range between 0.2 and 6 GHz. Throughout the entire frequency range this normal tissue is distinguishable from the abnormal tissue as shown by curve 202.

Figure 19:
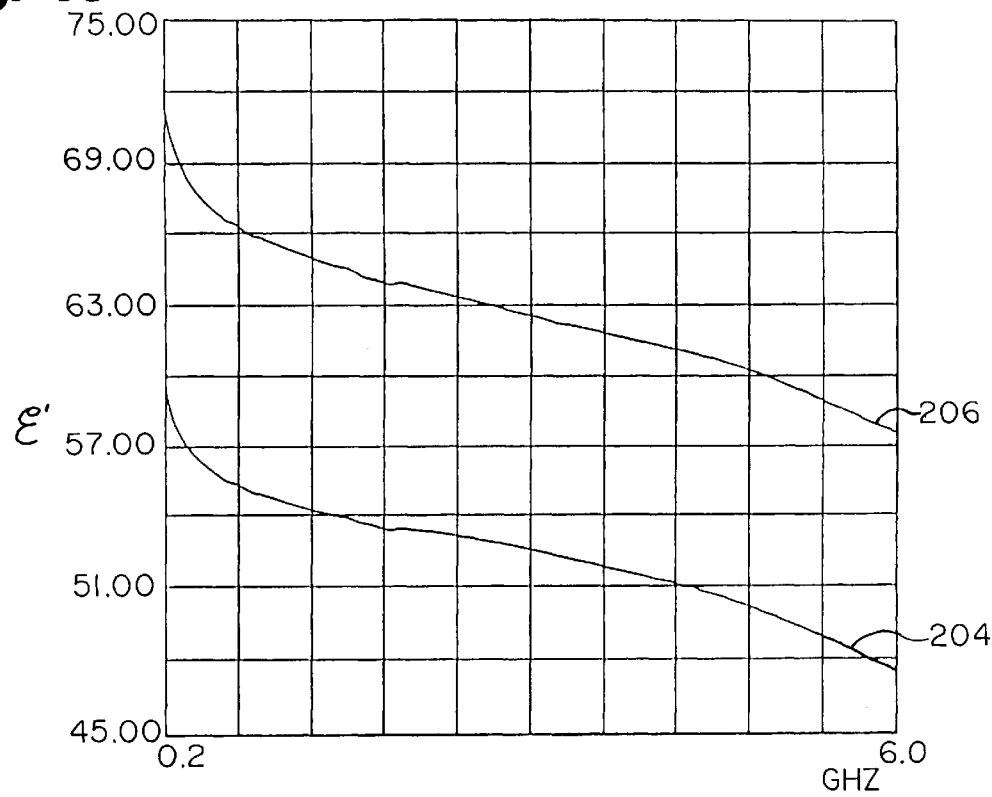
FIG. 19 is a graph of first order dielectric characteristics for a human left ventricular myocardium normal tissue to diseased tissue correlated by frequency of microwave emissions.

FIG. 19 shows the E' dielectric permittivity characteristic curves for this same tissue sample. Normal tissue has a E' single curve represented by curve 204. The abnormal tissue is shown in curve 206. The normal myocardial tissue is distinguishable from abnormal myocardial tissue over the entire microwave frequency range used in the present invention.

Figure 20:
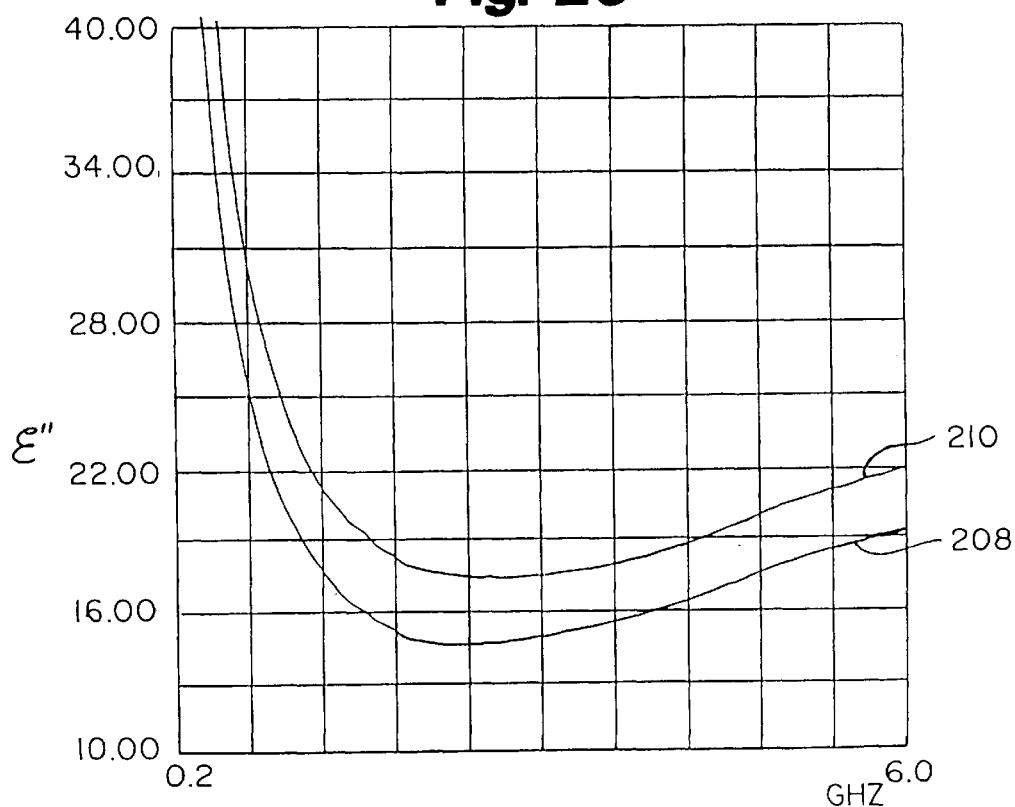
FIG. 20 is an expanded scale graph of the second order dielectric characteristics for a human left ventricular myocardium normal tissue to diseased tissue correlated by frequency of microwave emissions shown in FIG. 18.

FIG. 20 is an expanded scale graphic representation of the same E" dielectric loss data of FIG. 18. Curve 208 represents the e" for normal myocardial tissue with curve 210 representing the E" values for abnormal cardiac tissue.

The present invention is able to use this dielectric characteristic difference to generate an image. For example, as system 10 of FIGS. 1–4 scans a patient's chest, an anatomical image of the organs is obtained based on the dielectric characteristic differences between the various tissues as demonstrated in FIGS. 5–12 and 18–20. Additionally, the invention facilitate anatomical location of diseased abnormal tissue within normal tissue. This anatomical information is useful in many ways. An example of one important use would be to direct real time therapy. Often abnormal myocardial tissue causes deleterious rhythm disturbances. Unfortunately, this abnormal tissue may be visually indistinguishable from surrounding normal myocardium. The present invention provides real time imaging of the abnormal tissue based on the dielectric characteristic differences such as those detected in FIGS. 18–20. Using fast reconstruction routines and scanning through the frequency range in at time rates that are fractions of the tissue event time cycle, a clinician creates a map of the abnormal tissue. Depending upon which frequency and dielectric characteristic is evaluated, the investigator may reconstruct the dielectric properties to generate a functional excitation map through the abnormal tissue area or alternatively may reconstruct a temporal change map and correlate those temporal changes to known electrical markers for anomalies within the tissue. The clinician may then direct ablation therapy to remove this abnormal rhythm focus and evaluate the adequacy of the tissue removal.

Figure 21:
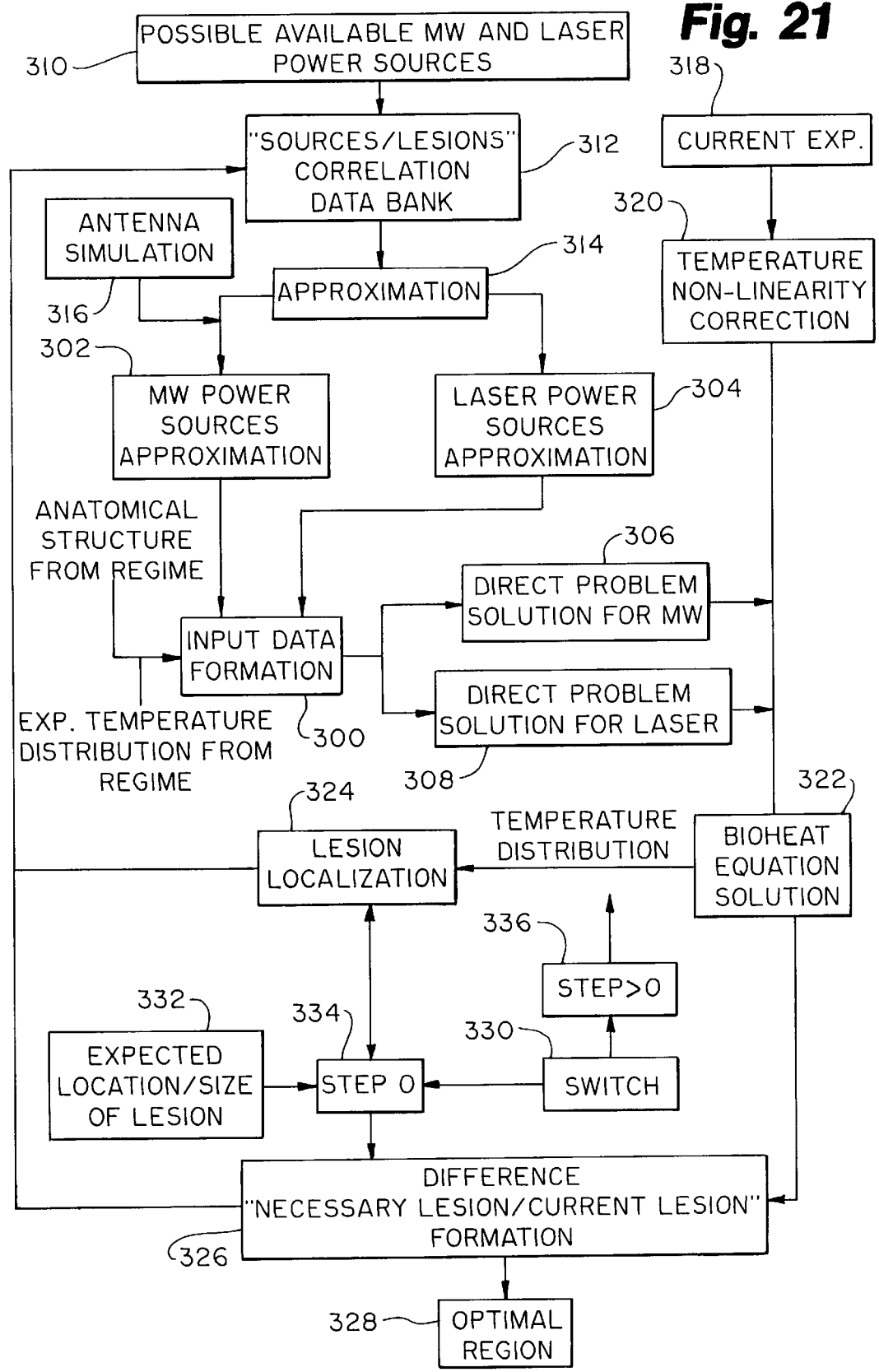
FIG. 21 is a flow diagram of an ablation choice algorithm.

An embodiment of the present invention using laser or microwave sources of ablation is disclosed in FIG. 21. As disclosed, a method for ablation of a lesion, for example, an arrhythmogenic focus within normal myocardial tissue, is performed beginning with inputting information into an input data formation step 300 from anatomical structure analysis derived from data generated by the invention disclosed in FIG. 2 and expected temperature distribution values. The input data formation step uses information from a microwave power source as an approximation step 302 or a laser power source as an approximation step 304 to derive input to be fed to a direct problem solution for microwave 306 or direct problem solution for laser control 308. A determination step for determining the possible available microwave and laser power sources is undertaken at step 310. The result of this determination is passed onto a sources and lesions correlation databank 312 to derive an approximation step 314, also taking input from an antenna simulation step 316. The current expected temperature is calculated at step 318 and corrected for a temperature non-linearity at step 320. The results of the direct problem solutions for microwave or laser 306, 308 in conjunction with the corrected current temperature from 320 is incorporated into a biological heat equation solution 322 to derive an actual temperature solution. Temperature distribution from the bioequation step 322 is passed to a lesion localization step 324 which provides data back to the source lesion correlation databank 312 for running the next approximation through to the input data formation 300 for the next determination of the bioheat equation solution step 322. Information from the equation solution step 322 is also passed to a different necessary lesion current lesion formation step for comparing the current lesion size with the estimated necessary lesion size to determine if optimum therapy has been achieved or not. If treatment has been achieved, the decision then passes to optimal region step 328. If the current lesion is different than the necessary lesion, the different information is passed back to step sources lesion correlation databank 312 for a reapproximation at step 314 on through input data formation 300 to undertake the next treatment in order to more closely approximate the necessary lesion through treatment. The number of steps through the iterative process are monitored by switch 330 with comparison of an expected location size of lesion step 332 at step 0, step 334. For steps greater than 0, switch 330 switches to step greater than zero step 336. The entire process is continuously re-evaluated for completeness of ablation therapy and re-evaluating on a real time basis the lesion generated by analysis of the anatomical structure derived from the microwave tomographic imaging system.

The above described system provides for using microwave energy in a novel approach providing rapid real time assessment of biological function and anatomical structure by reverse problem solution for the dielectric characteristics of biological tissues. The invention achieves substantial increase in processing speed as well as substantial improvement in resolving power over any known prior art. The present invention also provides for techniques in evaluating real time parameters for determining biological component concentrations or physiologic characteristics based on the dielectric contrast between different states of physiologic activity for the biological compound or physiologic reaction. Additional approaches to achieving the above advantageous results will be further described below, including modified iteration algorithms, low frequency (EIT) and microwave frequency as the multiple frequency combination, as well as new bulk myocardium dielectric analyses.

2. Review of Bulk Myocardium Dielectric Properties

In the process of discovering the various benefits and features of these inventions, the inventors have achieved several breakthrough techniques and accomplishments. In this regard, a preferred new model of bulk myocardium dielectric properties is being utilized. This model assumes a composition of membrane covered cells which are modeled as infinite cylinders. This model utilizes the complex values of dielectric properties of the intracellular, extracellular media and the cellular membrane. The model is useful to analyze the myocardial resistivity above and below the cell membrane relaxation spectrum in normal myocardium and in acute and chronic infarction. This myocardium cell model gives reasonable qualitative explanation not only for the spectrum of normal myocardial resistance but also for observed changes in the spectrum of myocardial resistance in acute ischemia and chronic infarction based on a volume fraction hypothesis.

The contributions of intracellular, extracellular and cell membrane resistances to bulk myocardial resistance are frequency dependent. At frequencies below 0.2 MHz the intracellular contribution to bulk resistance is much smaller compared to the extracellular resistance and does not exceed 10–15%. At frequencies higher than 0.5 MHz the measured bulk resistance reflects extracellular and intracellular resistances at about the same order. The contribution of the cell membrane resistance reflects extracellular and intracellular resistances at about the same order. The contribution of the cell membrane resistance is much smaller compared to the intracellular and extracellular resistances and does not exceed 0.1% at a frequency near 1 Hz for normal myocardium.

A specific experiment with these assumptions will be described below, in which significant changes in myocardial dielectric properties in acute and chronic myocardial infarction were detected at a spectrum near the cell membrane relaxation frequency. A theoretical explanation for the observed changes in bulk myocardial resistance in acute and chronic infarction is proposed here. This explanation is based on a new model of bulk myocardium dielectric properties as a composition of membrane covered cells modeled as infinite cylinders. This model utilizes the complex values of dielectric properties of the intracellular, extracellular media and the cellular membrane. The model was used to analyze the myocardial resistivity above and below the cell membrane relaxation spectrum in normal myocardium and in acute and chronic infarction. The reason for this is a principally different current flow pattern through and/or around cells at frequencies lower and higher than relaxation frequency of the cell membrane. The contributions of intracellular, extracellular and cell membrane resistances to measured bulk myocardial resistance were theoretically investigated also.

The term low frequency resistance or dielectric properties will, in this context, denote such properties at the frequency at or below 0.2 MHz. It is readily apparent that lower values may be chosen consistent with these concepts. The term reconstructed or high frequency resistance denotes the inverse value of the ion conductivity component determined from microwave frequency dielectrical spectrum data.

The ion conductivity part at high frequencies was reconstructed from measured dielectric properties at the microwave spectrum. This reconstruction was performed based on a multicomponent model, the myocardial dielectric properties in the microwave spectrum were described in a complex form as free water, bound water, and protein relaxations with corresponding volume fractions and ion conductivity.

For this purpose, consider a homogeneous medium with complex dielectric permittivity ($E_2$) in which some part of the volume is occupied by cells ($V_{cell}$) with certain geometrical shape (sphere or infinite cylinder with radius ($r_1$)). Each cell consists of two layers. Assume the outer layer is a homogeneous membrane with complex dielectric permittivity ($E_1$) and thickness (h) and a homogeneous intracellular media ($E_0$). Let us assume further that the cell concentration is small enough to neglect their interactions.

Myocardial histology shows that the cellular structure is close to cylinders connected with each other rather than spheres. Accordingly, this model utilized the cylindrical approach. This model also utilizes the complex values of dielectric properties. The Laplace equation for this model was solved under the assumption that cells are not interacting with each other. Effective dielectric properties of a mixture $E_{eff}$ were determined as a coefficient between mean (by volume) values D and E:

$$\overline{D} = \epsilon_{eff} \overline{E} \qquad \text{Equation (4)}$$

In this case of cylindrical or spherical cells, the equation for $E_{eff}$ can be rewritten as:

$$\varepsilon_{eff} = \frac{\int_v D(r) dr}{\int_v E(r) dr} = \varepsilon_1 + \frac{(\varepsilon_0 - \varepsilon_2) \int_{v_0} E(r) dr + (\varepsilon_1 - \varepsilon_2) \int_{v_1} E(r) dr}{\int_{v_0} E(r) dr + \int_{v_1} E(r) dr + \int_{v_2} E(r) dr} \qquad \text{Equation (5)}$$

Now consider electrically non-interacting cells and neglect the electrical field alteration in the extracellular space. Under these assumptions and taking into account that the directions of all mean electrical fields are similar and coincide with the direction of an external field (for example, x):

$$\overline{E^{(0)}}_x = A_o E^{hsc}; \quad \overline{E^{(1)}}_x = A_i E^{hsc}; \quad \overline{E^{(2)}}_x = E^{hsc}, \qquad \text{Equation (6)}$$

then a follow on equation for $E_{eff}$ can be rewritten as:

$$\varepsilon_{\it eff} = \varepsilon_2 + \qquad\text{Equation (7)}$$

$$V_{cell}\frac{(\varepsilon_0-\varepsilon_2)\frac{r_0^n}{r_1^n}\overline{E^{(0)}}+(\varepsilon_1-\varepsilon_2)\left(1-\frac{r_0^n}{r_1^n}\right)\overline{E^{(1)}}}{V_{cell}\frac{r_0^n}{r_1^n}\overline{E^{(0)}}+V_{cell}\left(1-\frac{r_0^n}{r_1^n}\right)\overline{E^{(1)}}+(1-V_{cell})\overline{E^{(2)}}}$$

Finally, the equation is obtained for the mixture (or bulk myocardial) complex dielectric permittivity:

$$\varepsilon_{mix} = \varepsilon_2[1 + nV_{cell}A/B] \qquad\text{Equation (8)}$$

Where: n=e for a sphere and 2 for an infinite cylinder, r0=r1−, and h is the internal cell radius, $$A = \Big[(\varepsilon_1-\varepsilon_2)(\varepsilon_0+(n-1)\varepsilon_1) + \qquad\text{Equation (9)}$$

$$(\varepsilon_0-\varepsilon_1)(\varepsilon_2+(n-1)\varepsilon_1)\frac{r_0^n}{r_1^n}\Big]$$

$$B = (\varepsilon_0+(n-1)\varepsilon_1)[(\varepsilon_1+(n-1)\varepsilon_2)+V_{cell}(\varepsilon_2-\varepsilon_1)] + \qquad\text{Equation (10)}$$

$$\frac{r_0^n}{r_1^n}(\varepsilon_0-\varepsilon_1)[(n-1)(\varepsilon_1-\varepsilon_2)-V_{cell}((n-1)\varepsilon_1+\varepsilon_2)]$$

The basis of the probe method described below (co-axial probe) is a measurement of complex input impedance of the probe, located on the surface of a semi-infinite media with dielectric constant E' and conductivity σ. An active and reactive component of input probe impedance at a certain frequency can be described as:

$$R_{inp} \sim \int_v \sigma|\overline{E}|^2 dv + \int_s \overline{E}\times\overline{H}ds \qquad\text{Equation (11)}$$

$$X_{inp} \sim \int_v (\mu|\overline{H}|^2 + \varepsilon|\overline{E}|^2)dv$$

Keeping in mind that the first term of the active part of the complex input impedance reflects an active loss in the tested medium, it is possible to estimate the contribution of intracellular, extracellular and membrane resistivities to the bulk resistance:

$$Contribution_i \sim \int_{v_1}\sigma_i|\overline{E}|^2 dv \quad i=0,1,2 \qquad\text{Equation (12)}$$

where: i=0 for intracellular; i=1 for membrane; and i=2 for extracellular.

For the theoretical calculation of bulk myocardial resistance at low and high frequencies using this model the following parameters were used: extracellular resistance $R_{ext}$=70 ohm*cm, intracellular resistance $R_{int}$=185 ohm*cm, membrane resistance $R_{mem}$=1 Kohm*cm2, membrane capacitance $C_{mem}$=1 μF/cm2, cell radius $R_{cell}$=10 μm, extracellular and intracellular dielectrical values $E_{int}=E_{ext}$=75. The cellular volume fraction $V_{cell}$ and frequency can be varied.

It is important to understand the contribution of both extracellular and intracellular resistances to the measured bulk myocardial resistance. The values for the contribution of extracellular and intracellular resistances at normal myocardium cellular volume fraction ($V_{cell}$=0.75) are summarized in Table 1.

TABLE 1

Frequency dependence of extracellular and intracellular contributions [%] to bulk myocardium resistance.

| Frequency | 1 Hz | 10 kHz | 100 kHz | 0.5 MHz | 1 MHz | 1 GHz |
|---|---|---|---|---|---|---|
| Intracell | 7.7 | 7.7 | 10.3 | 41.1 | 60.5 | 66.3 |
| Extracell | 92.2 | 92.2 | 89.6 | 58.9 | 39.5 | 33.7 |

As can be seen from Table 1, the contribution of intracellular resistance is much smaller when compared with extracellular resistance at low frequencies. It becomes negligibly small at a low cellular volume fraction. At the same time at high frequencies the contributions of intracellular and extracellular resistances are almost equal at a normal cellular volume fraction. Therefore the bulk resistance of the normal myocardium measured by the low frequency means of the invention reflects mostly extracellular resistance (from DC up to 0.2 MHz). For frequencies higher than 0.5 MHz the measured bulk resistance reflects extracellular and intracellular resistances at about the same order.

The membrane resistance contribution to bulk myocardium resistance is much smaller when compared with the extracellular and intracellular resistances. For example, at a normal cellular volume fraction (near 0.70–0.75) the membrane contribution at the frequencies 1 Hz, 1 MHz and 1 GHz is 0.1%, 0.02% and about $1\times10^{-6}$% respectively. It should be emphasized that the model does not take into account an alteration of the electromagnetic field caused by cell to cell interaction. The gradient of the electromagnetic field across a membrane is quite large in lower frequencies. It decreases with increasing frequency and becomes negligible after the relaxation frequency region (1–10 MHz). It is consistent with a well known phenomenon that the amplitude of a stimulation current is proportional to frequency. It can be predicted that stimulation by externally applied currents (as contemplated by embodiments of this invention) is almost impossible at frequencies higher than 10 MHz and for a reasonable current amplitude.

It should be pointed out that the electromagnetic field distribution in the myocardium is quite different using the contact probe in the initial phases of this method than in any form of invasive probes placed into the myocardium. The mean values of experimentally measured resistances are compared with the theoretically predicted myocardial resistances for this model at body temperature and are summarized in Table 2.

TABLE 2

The mean values of canine LV myocardial resistance in situ.

|  | $\rho_{mw}$ [ohm*cm] | $\rho_{LF}$ [ohm*cm] |
|---|---|---|
| Experiment | 133 ± 17 | 202 ± 13 |
| Theory (Vcell = 0.7) | 130-sphere; | 247-sphere; |
|  | 132-inf. cylinder | 286-inf. cylinder |

As can be seen from Table 2, experimentally measured and theoretically predicted values of normal myocardial resistance reasonably agree, particularly at microwave frequencies assuming a cellular volume fraction of 0.7 for both spherical and cylindrical modeling. An increase of myocardial resistance after 2 hours LAD occlusion is summarized in Table 3, comparing measured values at high and low frequencies with those predicted by this model.

TABLE 3

The changes of canine myocardial resistance after 2 hours LAD occlusion.

|  | $\Delta\rho_{mw}$ [%] | $\Delta\rho_{LF}$ [%] |
|---|---|---|
| Experiment | 12 ± 9 | 42 ± 21 |
| Theory ($\Delta V$cell = +0.15%) | 19-sphere; 18-inf. cylinder | 65-sphere; 62-inf. cylinder |

As can be seen from Table 3, this myocardial cell model gives a reasonable explanation of observed changes in the spectrum of myocardial resistance in acute ischemia based on the volume fraction hypothesis. As further discussed below, measurements were performed for myocardial dielectric properties on four 3 week chronic myocardial infarction cases which resulted in an observed decrease in myocardial resistivity of about 30% and 10% for frequencies lower and higher than cell membrane relaxation frequency respectively. Recognizing that the amount of myocytes in a chronic aneurysm is very small as compared with collagen, and assuming that the myocardial cellular volume fraction decreases down to 0.2 in an aneurysm. In this case the theoretical calculation gives the following values of resistances:
$\Delta\rho_{mix}^{thr}=-20\%$ and $\Delta\rho_{LF}^{thr}=-66\%$ for sphere and $\Delta\rho_{LF}^{thr}=-68\%$ for cylinder. Finally, this myocardium cell model gives reasonable qualitative explanation not only for the spectrum of normal myocardial resistance but also for observed changes in the spectrum of myocardial resistance in acute ischemia and chronic infarction based on the volume fraction hypothesis.

This theory reasonably predicts the normal myocardial bulk resistance. Experimentally measured values of bulk myocardial resistivity and E' in two different spectrum ranges can be interpreted by the model. It can be done in such a way that the model parameters (such as intracellular, extracellular and membrane resistance, cellular volume fraction and cellular capacitance) can be theoretically reconstructed from experimentally measured bulk myocardial resistivity and dielectric properties.

3. Review of Canine Experiments

A study of canines was performed using a coaxial probe method of measuring myocardial resistance based on the measurement of tissue dielectric properties, and reconstruction from that data. The probe utilized is located on the surface of the epicardium and is used to measure the dielectric properties of the myocardium. It is also important from the tomographic imaging perspective of this invention that the dielectric properties measured by this method, and the reconstructed myocardial resistance, are potentially the same as can be reconstructed by tomography. In both cases the basis for the determination of the dielectric properties is the interaction of an external electromagnetic field with tissue, and the measurement of a scattered (reflected) electromagnetic filed. Therefore, experimental data received by the probe method can be directly utilized for interpreting tomographic data. The application of experimental data obtained by the methods of invasive probes delving into the myocardium is not so readily useful.

This canine study focused on changes of the myocardial E' and resistance at frequency spectra lower and higher than the cell membrane relaxation frequency. The reason for this is a principally different current flow pattern through and/or around cells at frequencies lower and higher than the relaxation frequency of the cell membrane. The real part E' of complex dielectric permittivity for high frequency is determined as measured at a frequency of 0.2 GHz.

Animals used in the study were part of an Institutional Animal Care and Use Committee approved research protocol and cared for under NIH guidelines for laboratory research. Four canines underwent total left anterior descending coronary artery (LAD) occlusion for two hours. First, the whole studied spectrum of myocardial dielectric properties (in this instance from 0.1 MHz up to 6.0 MHz) was measured. After 15 minutes of baseline dielectric measurements (from 0.2 to 6.0 MHz), local myocardial temperature and dielectric properties were measured immediately after occlusion, and following 2 hours of blood flow arrest. At the end of the 2 hour occlusion whole spectrum measurements were repeated.

The effect of chronic myocardial infarction on the myocardial dielectric properties was studied in four canines 3 weeks after myocardial infarction. The same anesthetic and surgical protocol was followed as in the acute experiments.

At high frequencies (from 0.2 GHz to 6.0 GHz) dielectric properties were measured with the aid of a Hewlett-Packard network analyzer (HP model 8753C). At low frequencies (from 50 kHz to 2 MHz) dielectric properties were measured with the help of a specially manufactured device for complex impedance measurements, which is part of the above invention for electrical impedance tomography.

All values are expressed as mean±one standard deviation. Data was analyzed using Statgraphics version 4.0/T-test software.

Figure 22:
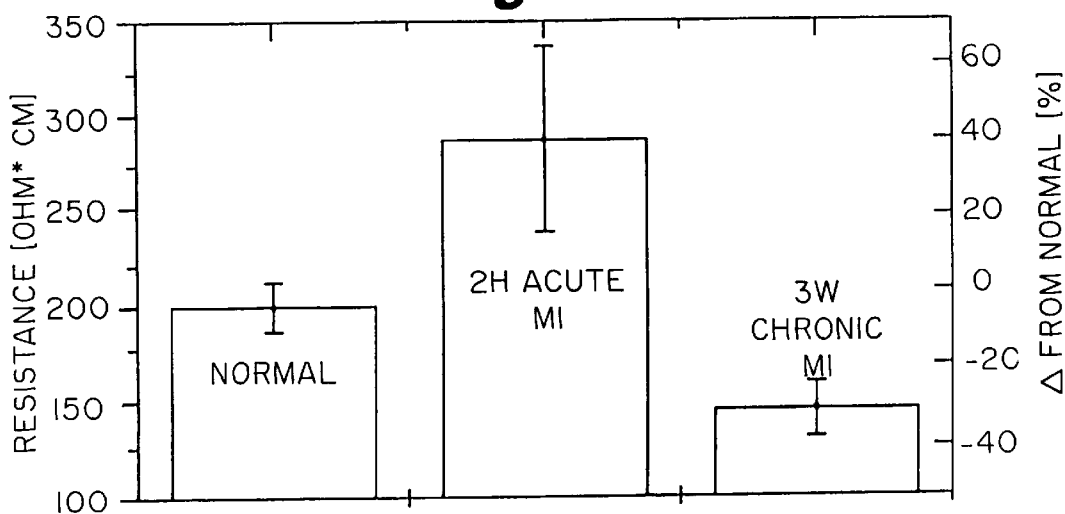
FIG. 22 is a chart of dielectric properties at normal, acute and chronic ischemias.
Figure 23:
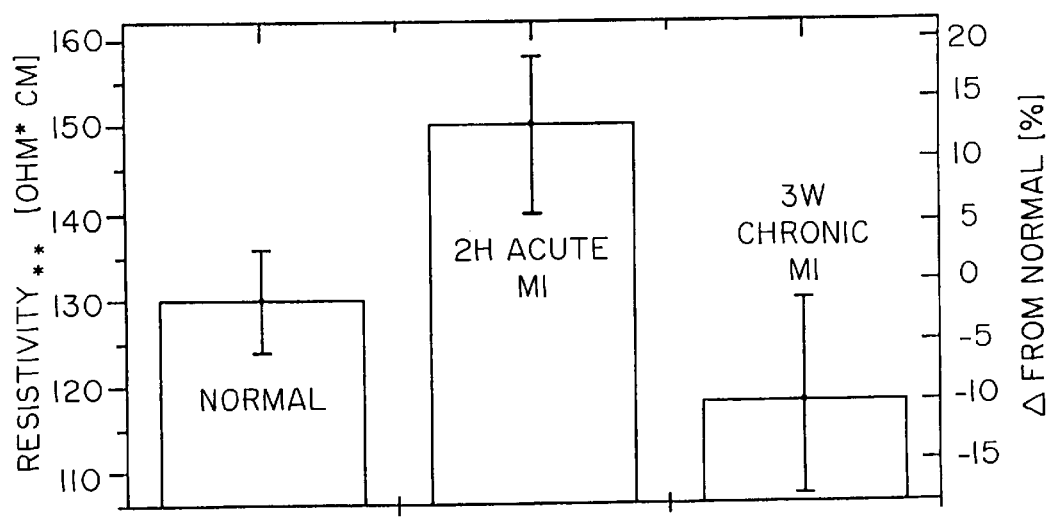
FIG. 23 is a chart of dielectric properties at normal, acute and chronic ischemias.

The contributions of extracellular, intracellular and membrane resistances to measured bulk myocardial resistivity are quite different at frequencies lower and higher than a cell relaxation frequency. It was expected that changes in myocardial dielectric properties in acute and chronic infarction would also be different. Changes of myocardial resistivity in acute and chronic infarction are summarized for frequencies lower (FIG. 22) and higher (FIG. 23) than a cell membrane relaxation frequency.

At high frequencies a cell membrane is essentially "invisible" and the reconstructed ion conductivity will reflect both intracellular and extracellular conductivities with a certain ratio influenced mostly by the cellular volume fraction. At lower frequencies the measured resistance will mostly reflect ion conductivity properties of the extracellular space, principally because of a relatively low membrane conductivity. As expected, changes at low and high frequencies are in the same direction but differ in magnitude. In acute ischemia, myocardial resistivity significantly (Sign. Lev. 0.02 and 0.01) increased in both frequencies up to about 42% and 14% respectively for low and high frequencies. Three weeks chronic myocardial infarction causes a decrease of bulk resistance to about 30% and 10% for low and high frequencies.

Observed changes in myocardial resistivity can be explained on the basis of a cellular volume fraction hypothesis. It is well known that myocardial resistance increases in acute ischemia. In these experiments, an almost instantaneous increase in bulk myocardial resistance after a coronary flow arrest was observed. Prior researchers showed that arrest of coronary flow resulted in an almost immediate increase in extracellular resistance, but that it was due likely to a decrease in intravascular volume. Based on that hypothesis the observed changes of myocardial resistance can be understood. Indeed, in the case of low frequency measurements, by the probe method used by the inventors, bulk myocardial resistance mostly reflects an extracellular resistivity, while much higher changes were observed when compared with the case of high frequency, where measured bulk myocardial resistance reflects both extracellular and intracellular resistivities in about the same order. Observed changes in myocardial resistivity in 3 weeks chronic myocardial infarction can be explained as a decrease in cellular volume fraction.

Figure 24:
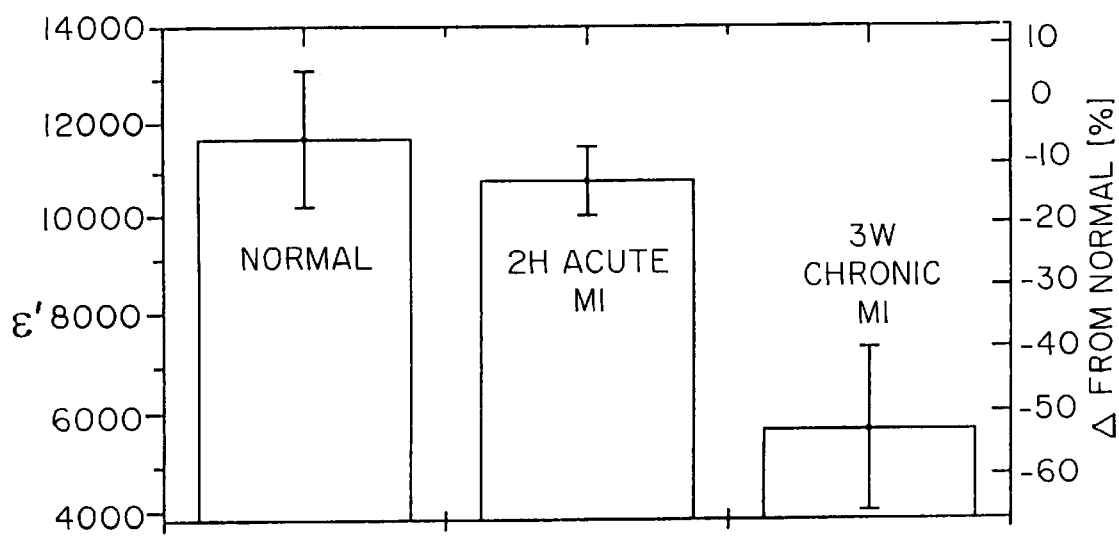
FIG. 24 is a chart of dielectric properties at normal, acute and chronic ischemias.
Figure 25:
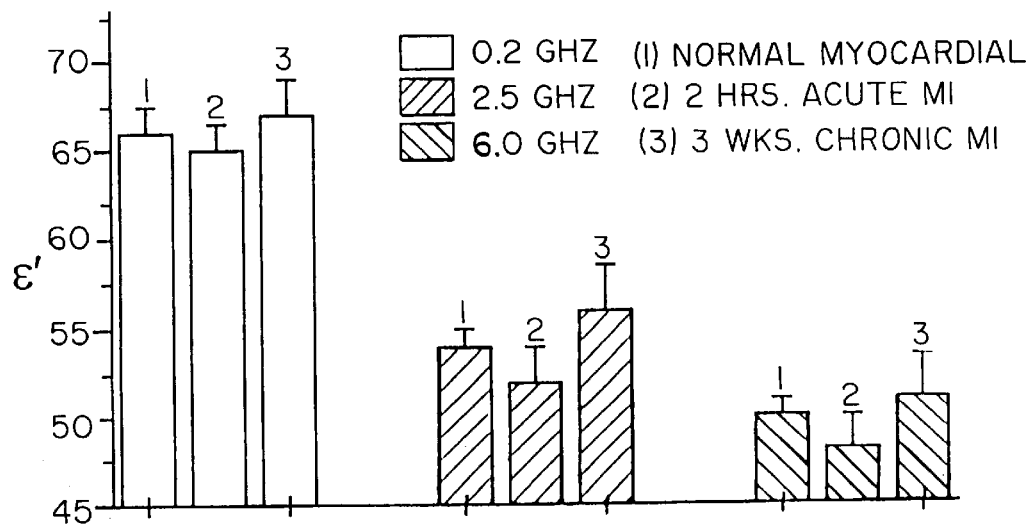
FIG. 25 is a comparison chart of dielectric properties at normal, acute and chronic ischemias.

In both acute and chronic myocardial infarction E' decreases in low frequency (FIG. 24). The magnitude of E' decrease was much higher in the chronic case-up to 52%. The changes of E' at high frequencies are presented in FIG. 25. In acute ischemia high frequency E' decreases in different magnitude and dynamic at different frequencies. In chronic infarction high frequency E' increases.

The inventors hypothesized that observed changes of E' at low frequency reflect the myocardial cell membrane dilution. At high frequencies observed changes of E' reflect complexity of events including cell membrane dilution, changes in tissue free and bound water composition, and protein restructuring. This experimental data proves that acute and chronic myocardial infarction causes significant changes of myocardial dielectric properties at a cell membrane relaxation spectrum. The observed changes in myocardial dielectric properties reflect a wide spectrum of biophysical events. The need to assess these changes in a real time multiple frequency environment is critical to enable use of such valuable information.

Figure 26:
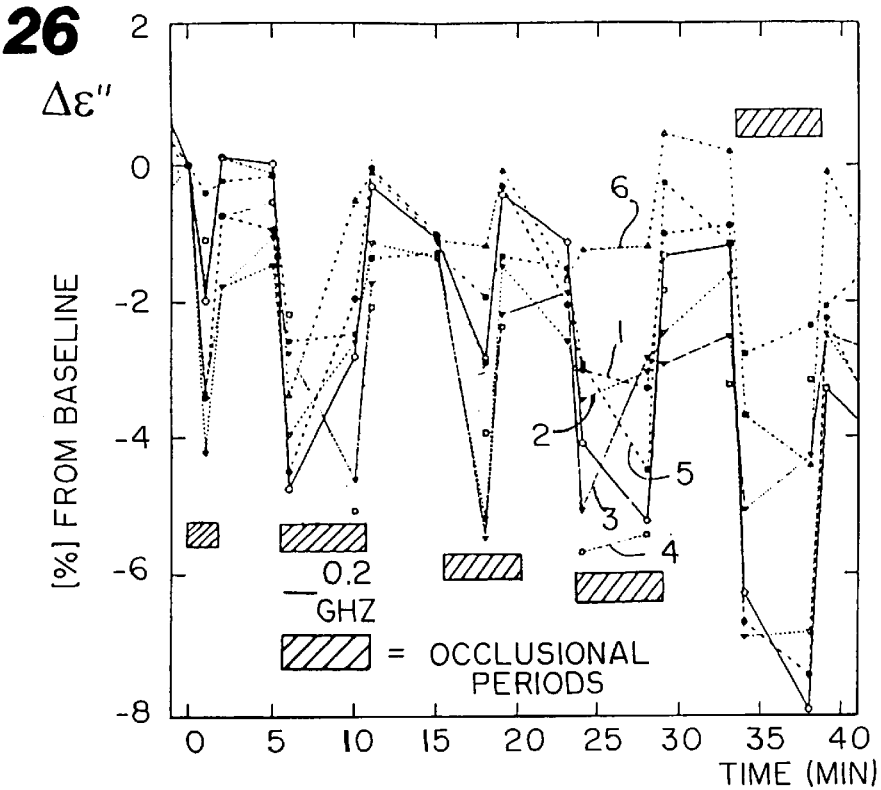
FIG. 26 is a chart of dielectric properties at periods of occlusion and reperfusion.
Figure 27:
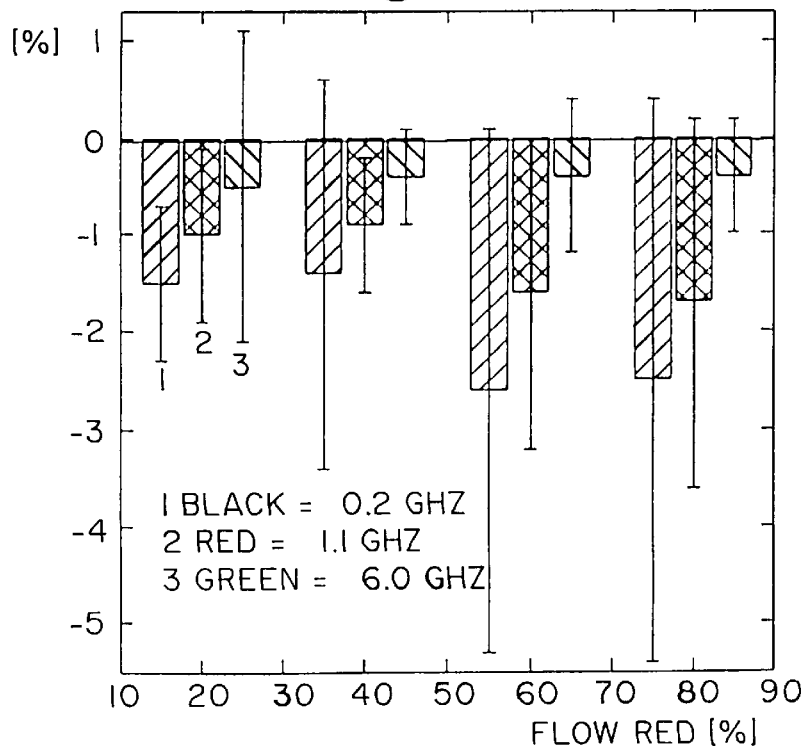
FIG. 27 is a chart of multiple frequency flow reduction of E".

Additional experimental evidence of these phenomena are shown in the following Figures. FIG. 26 shows the changes of myocardium dielectric properties followed by the LAD occlusion-reperfusion. In this figure, the tissue was assumed normal at time 0, and then merely ischemied rather than permanently damaged. FIG. 27 illustrates, for 10 canines experiencing decreased blood flow, the sensitivity of dielectric properties to measurement at different frequencies. This also shows the low frequency sensitivity of E". FIG. 28 shows a pre-occlusion (control) and occlusion relative changes of E' at time 0 across multiple frequencies. FIG. 29 is similar conditions to that of FIG. 28 but for E".

Figure 30:
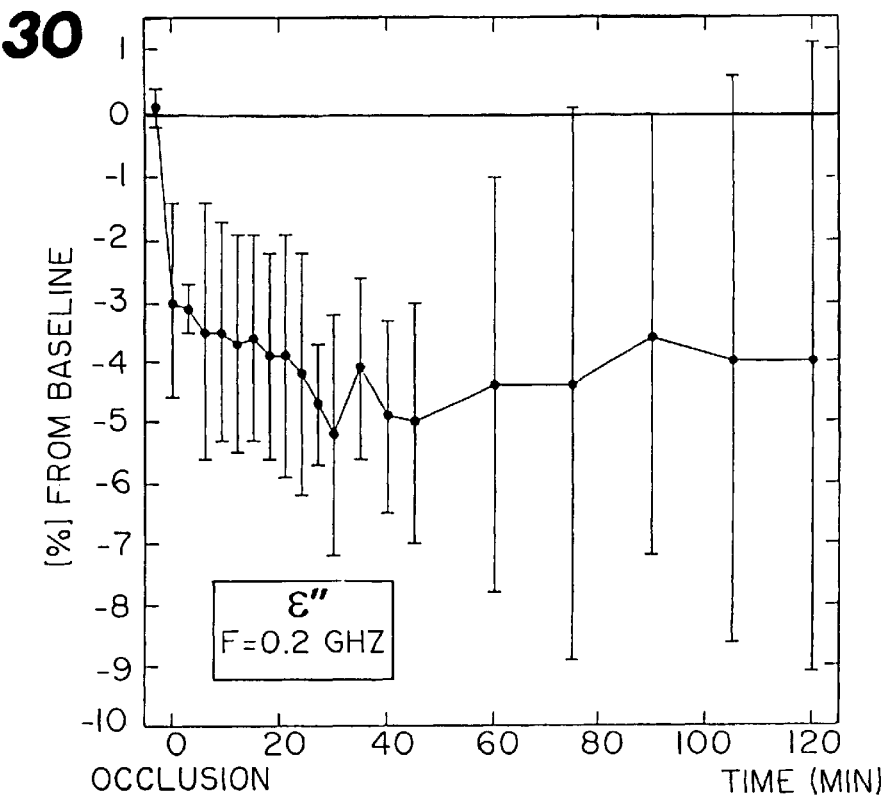
FIG. 30 is a chart of E" at a low frequency after occlusion.
Figure 31:
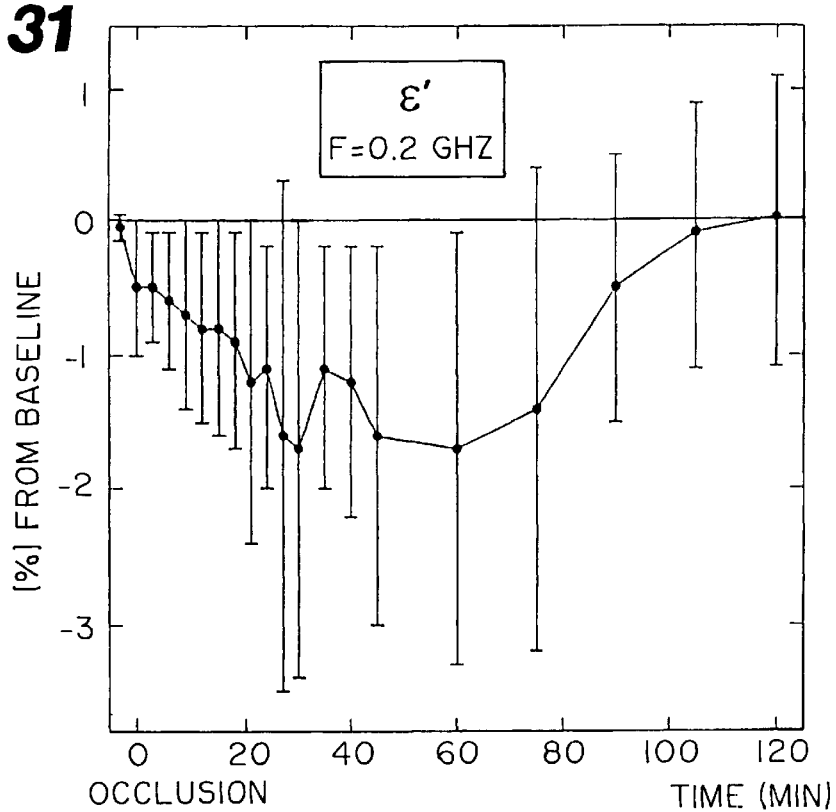
FIG. 31 is a chart of E' at a low frequency after occlusion.
Figure 32:
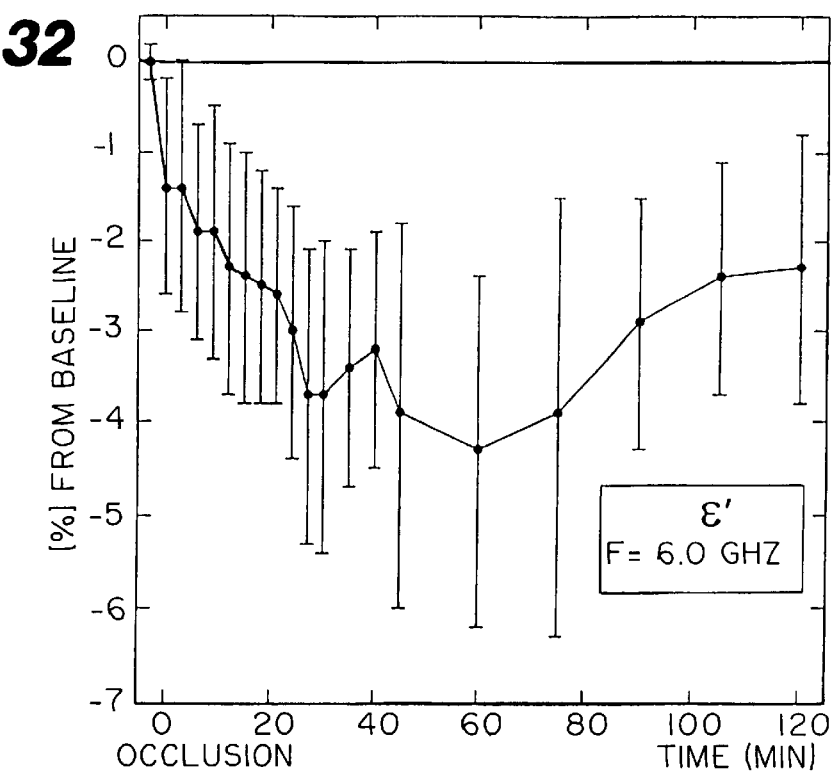
FIG. 32 is a chart of E' at a high frequency after occlusion.
Figure 33:
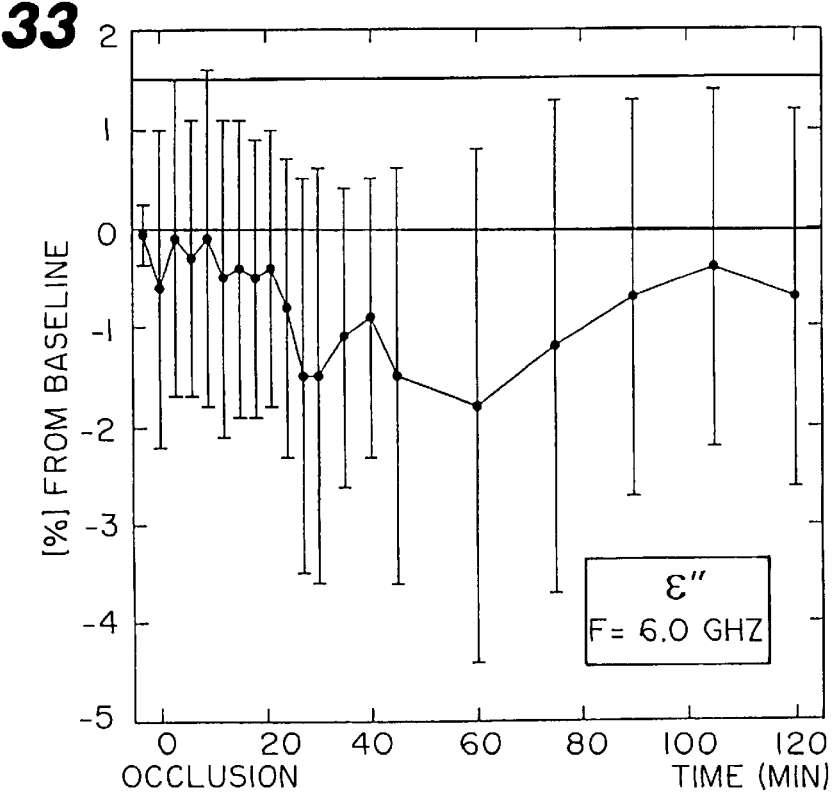
FIG. 33 is a chart of E" at a high frequency after occlusion.

In FIG. 30, the changes of myocardium dielectric properties for E" are shown following a 100% occlusion, detected by a 0.2 GHz frequency. This illustrates the dramatic and apparently irreversible changes occurring at the cellular level. This type of detection is not available in a real time basis by other techniques, such as by nuclear magnetic resonance. FIG. 31 also shows the myocardium properties following a 100% LAD occlusion, but for E' rather than E". As shown, the most dramatic changes are within the 30–40 minutes of the occlusion, which is also the approximate period during which most changes develop from reversible to irreversible. For example, in looking at the same E' but with a frequency of 6.0 GHz as shown in FIG. 32, one can see the changes as not returning to a baseline level, i.e. irreversible change having occurred in the myocardium. Finally, in FIG. 33, the E" value at 6.0 GHz is observed as almost returning to baseline over time. The ability to distinguish and predict the onset of different types of myocardial change through this and related modeling techniques is one of the advantageous outcomes of this invention.

Figure 34:
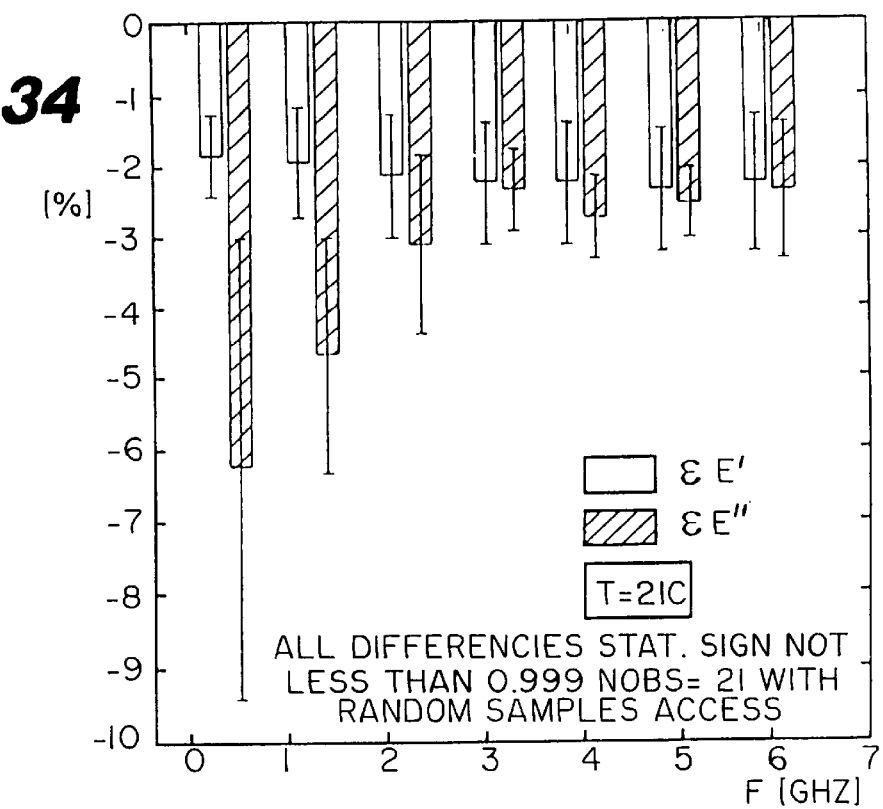
FIG. 34 is a comparison chart of dielectric properties at different frequencies.
Figure 35:
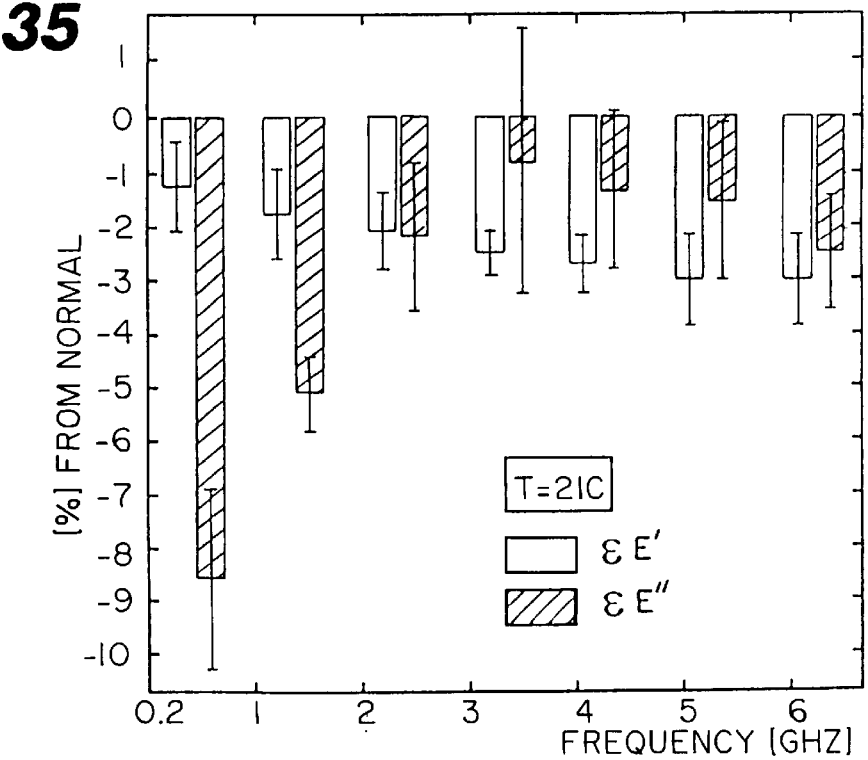
FIG. 35 is a comparison chart of dielectric properties at different frequencies.
Figure 36:
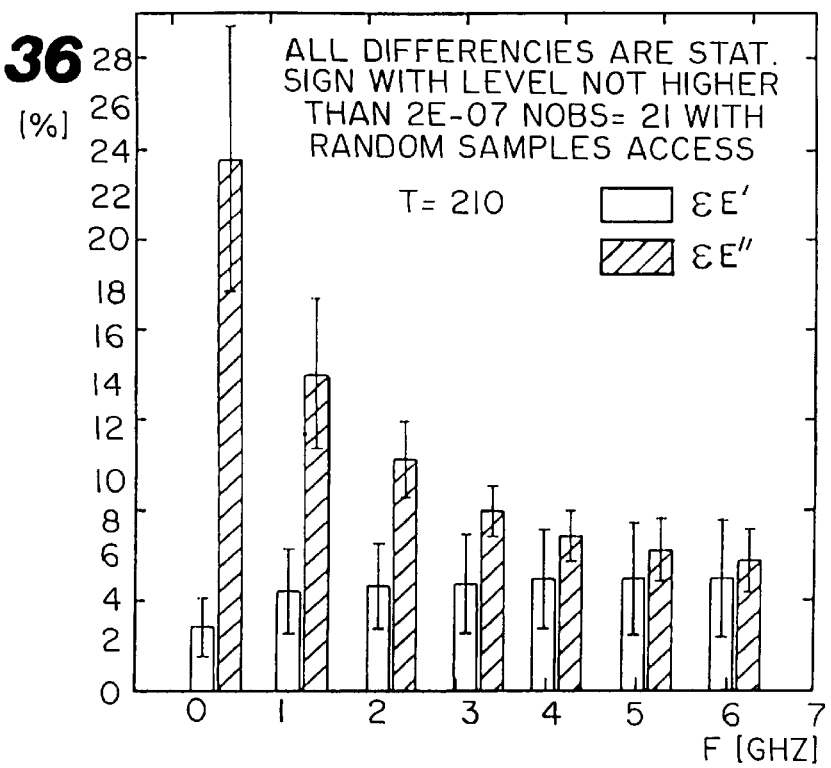
FIG. 36 is a comparison chart of dielectric properties at different frequencies.
Figure 37:
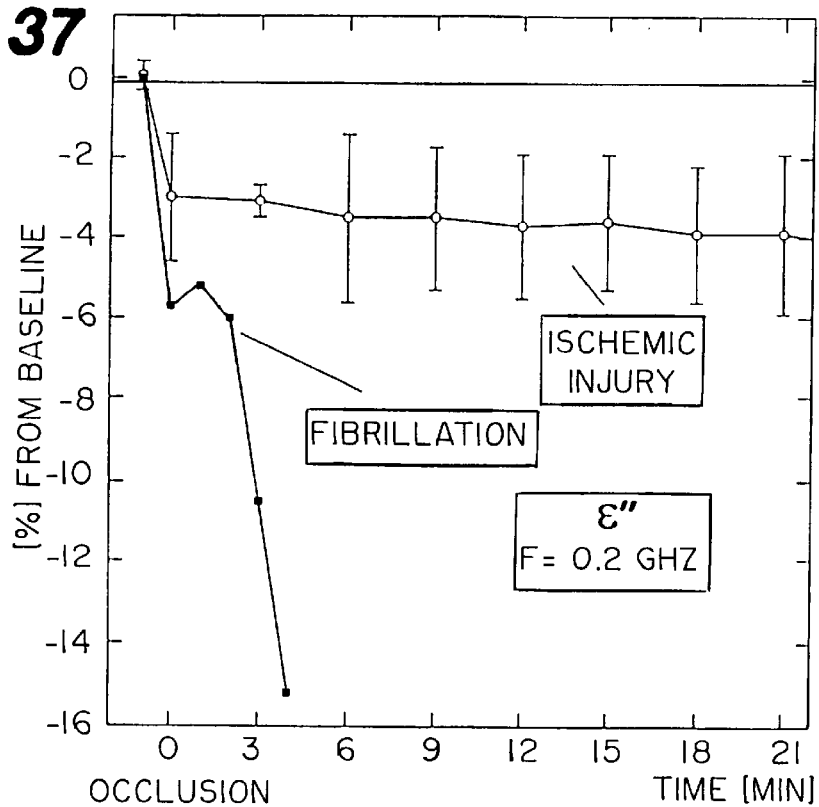
FIG. 37 is a comparison chart of dielectric properties over time at a low frequency.
Figure 38:
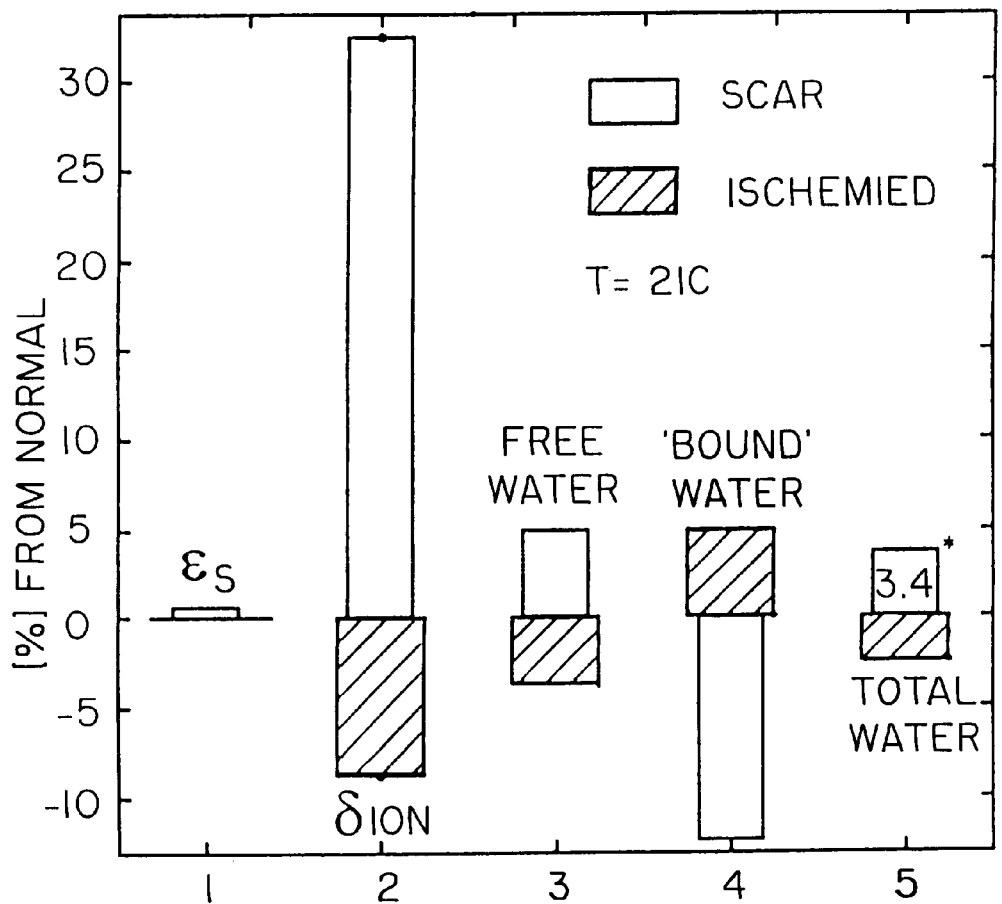
FIG. 38 is a comparison chart of dielectric properties.

In building the models for accurate biophysical reconstruction, it is helpful to analyze the normalized differences between ischemied and normal myocardium (FIGS. 34–35), scar and normal myocardium (FIG. 36), and markers to indicate whether fibrillation or ischemic injury is occurring (FIG. 37). In this manner the inventors are making it possible to create certain detection algorithms given certain patterns or gradients which aid the physician in a choice of possible treatment paths. The invention is also useful in localizing and displaying an infarcted region which may cause dangerous arrhythmia. Indeed, as shown in FIG. 38, the inventors' multiple frequency tissue experiments of dielectric properties allow reconstruction for E' and E" which effectively models various cellular phenomena. This greatly facilitates the determination of time since a tissue event, and the possible susceptibility of that tissue to further danger. For example, this helps isolate the region of scar versus ischemic tissue to enhance predictability of tissue electrical viability.

4. Spatial Improvements and Reconstruction Algorithms

Figure 39:
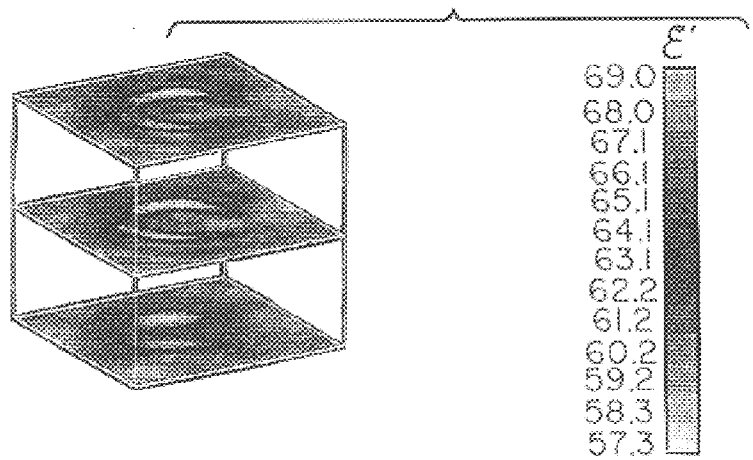
FIG. 39 is a reconstruction of E' of a beating heart.
Figure 40:
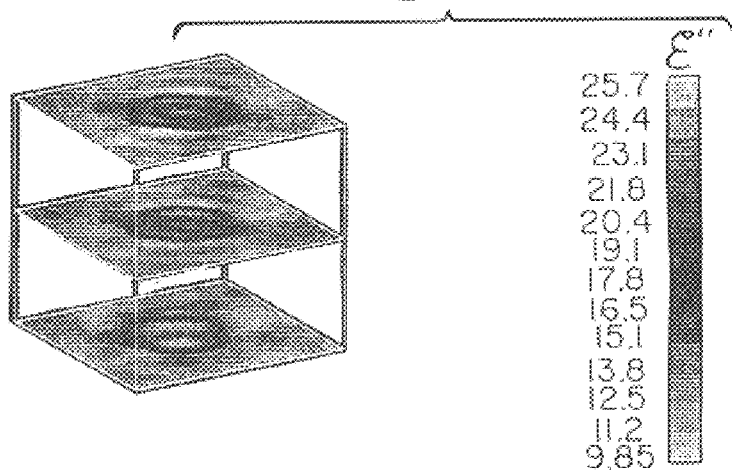
FIG. 40 is a reconstruction of E" of a beating heart.
Figure 41:
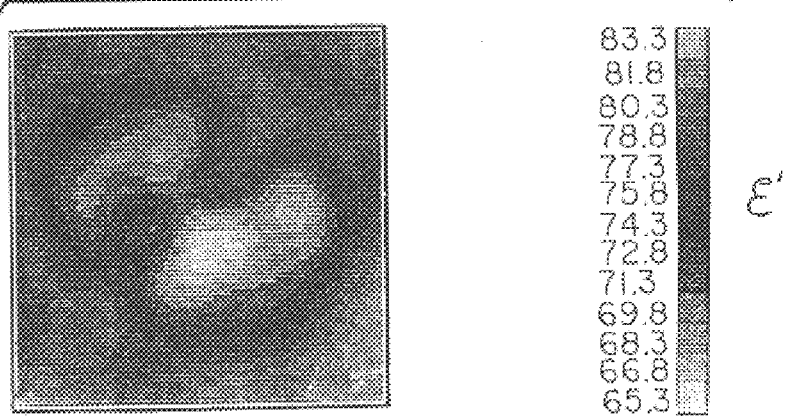
FIG. 41 is a reconstruction of E' of a non-beating heart
Figure 42:
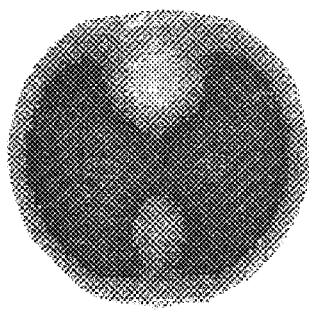
FIG. 42 is a reconstruction of E' of a first iteration of a gel phantom.
Figure 43:
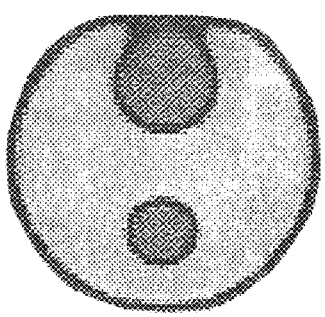
FIG. 43 is a reconstruction of E" of a first iteration of a gel phantom.
Figure 44:
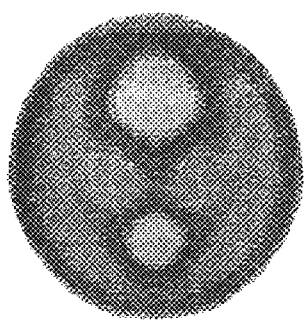
FIG. 44 is a reconstruction of E' of a tenth iteration of a gel phantom.
Figure 45:
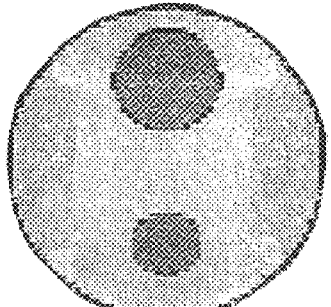
FIG. 45 is a reconstruction of E" of a tenth iteration of a gel phantom.
Figure 46:
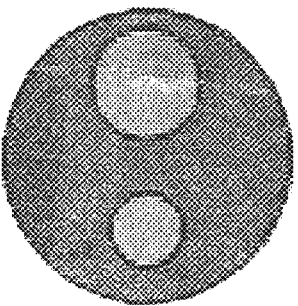
FIG. 46 is a reconstruction of E' of a 10% contrast mathematical model of a gel phantom.
Figure 47:
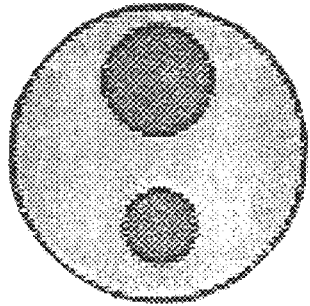
FIG. 47 is a reconstruction of E' of a 10% contrast mathematical model of a gel phantom.

The system and its various capabilities described above has been useful in imaging both phantom objects as well as actual tissue. Such tissue has included beating and non-beating heart reconstructions as shown in FIGS. 39–41. The spatial and contrast resolution experienced with the present system is influenced by the number of antennas, the mathematical reconstruction algorithms, and 2-D diffraction model utilization for 3-D scattering objects. Additional factors which influence the image quality include accuracy of the scattered field measurements, dielectric contrast, and various others. While various improvements can be noted, for example as shown in the iterations of a gel phantom at FIGS. 42–47, the overall improvements of this system involve a combination of multiple high and low frequencies, exceptional biophysical modeling and reconstruction, and system processing gains.

What is claimed is:

1. A method of detecting the onset of biological tissue disease comprising the method of:

a) designating a target tissue area for electromagnetic irradiation;

b) determining expected tissue dielectric values for the designated target tissue area at frequencies above and below the relaxation frequency of the designated target tissue;

c) providing a multiple frequency radiation emitting and receiving system having emission means comprising a plurality of emitter-receiver locations, receiving means comprising a plurality of emitter-receiver locations, and signal analysis means;

d) irradiating the target tissue area with the multiple frequency radiation emitted from a plurality of emitter-receiver locations, said multiple frequency radiation being suitable for discreet detection of intracellular, extracellular and cell membrane resistances;

e) receiving the radiation from the irradiated target tissue area with the microwave receiving means; and f) analyzing the received radiation with the signal analysis means to obtain observed tissue dielectric values an comparing the observed tissue dielectric values for a desired range of frequencies best correlating to the target tissue with the expected tissue dielectric values to determine a change in the physiologic state of the target tissue indicative of an onset of tissue disease.

2. The method of claim 1 in which the multiple frequency radiation is preferably within a range of about 100 kHz to about 6 GHz.

* * * * *